United States Patent
Yan et al.

(10) Patent No.: US 10,724,051 B2
(45) Date of Patent: Jul. 28, 2020

(54) METHODS FOR ENRICHING GENE-TARGETED CELLS

(71) Applicant: Institute For Cancer Research, Philadelphia, PA (US)

(72) Inventors: Hong Yan, Philadelphia, PA (US); Shuren Liao, Philadelphia, PA (US)

(73) Assignee: Institute For Cancer Research, Philadelphia, PA (US)

( * ) Notice: Subject to any disclaimer, the term of this patent is extended or adjusted under 35 U.S.C. 154(b) by 0 days.

(21) Appl. No.: 15/726,531

(22) Filed: Oct. 6, 2017

(65) Prior Publication Data

US 2018/0100167 A1   Apr. 12, 2018

Related U.S. Application Data

(60) Provisional application No. 62/405,540, filed on Oct. 7, 2016.

(51) Int. Cl.
| | | |
|---|---|---|
| *C12N 15/00* | (2006.01) | |
| *C12N 15/90* | (2006.01) | |
| *C12N 9/10* | (2006.01) | |
| *C12N 15/11* | (2006.01) | |
| *C12N 15/113* | (2010.01) | |

(52) U.S. Cl.
CPC ......... *C12N 15/907* (2013.01); *C12N 9/1077* (2013.01); *C12N 15/11* (2013.01); *C12N 15/1137* (2013.01); *C12Y 204/02008* (2013.01); *C12N 2310/20* (2017.05); *C12N 2320/34* (2013.01)

(58) Field of Classification Search
None
See application file for complete search history.

(56) References Cited

PUBLICATIONS

Liao et al, entitled "Enriching CRISPR-Cas9 targeted cells by co-targeting the HPRT gene" (Nucleic Acids Research, 2015, vol. 43, No. 20, pp. 1-8 (Year: 2015).*

Liao S., et al., "Enriching CRISPR-Cas9 targeted cells by co-targeting the HPRT gene", Nucleic Acids Res., 2015, 43 (20), pp. e134.

* cited by examiner

*Primary Examiner* — Catherine S Hibbert
(74) *Attorney, Agent, or Firm* — Stradley Ronon Stevens & Young, LLP

(57) ABSTRACT

A gene of interest and the gene encoding hypoxanthine-aminopterin-thymidine (HPRT) can be co-targeted for Casp9 nuclease-mediated editing or alteration in a cell. Based on whether the HPRT gene is altered to encode a non-functional protein, or is not so-altered, the co-targeted cells can be selected and counter-selected. HPRT co-targeting can be used to sequentially disrupt as many genes of interest as cell viability permits.

20 Claims, 16 Drawing Sheets
Specification includes a Sequence Listing.

c.

d.

e.

HPRT-wt
CCAGACTGTAA    TGCCCCTGTAGTCTCTCTGTATGTTATATGTCACATTTTGTAATTAACAGCTTGCTGGTGAAAAGGACCCCACGAAGTGTTGGATATAAG

HPRT Edited
CCAGACTGTAA    TGCCCTGTA--------------TATGTCACATTTTGTAATTAACAGCTTGCTGGTGAAAAGGACCCCGCGGTCTGTTGGATATAAG HPRT-hr Donor
CCAGACTGTAA    TGCCCTGTA--------------TATGTCACATTTTGTAATTAACAGCTTGCTGGTGAAAAGGACCCCGCGGTCTGTTGGATATAAG
*******      *****              **********************************************   ***************

HPRT-wt
GAGAGGCAC      GTGAATTACTTTTTTGTCAATCATTAACCATCTTTAACCTAAAAGAGTTTTATGTGAAATGGCTTATAATTGCTTAGAGAATATTTGTA

HPRT Edited
GAGAGGCAC      GTGAATTACTTTTTTGTCAATCATTAACCATCTTTAACCTAAAAGAGTTTATGTGAAATGGCTTATAATTGC------------------

HPRT-hr Donor
GAGAGGCAC      GTGAATTACTTTTTTGTCAATCATTAACCATCTTTAACCTAAAAGAGTTTATGTGAAATGGCTTATAATTGC------------------
*******      *********************************************************************

```
                                                          gRNA3-hr
HPRT-hr         TGCCCTGTA-------------TATGTCACATTTTGTAATTAACAGCTTGCTGGTGAAAAGGACCCCGCGGTCTGTTGGATATAAG
CCAGACTGTAA

HPRT Edited     TGCCCTGTAGTCTCTCTGTATGTTATATGTCACATTTTGTAATTAACAGCTTGCTGGTGAAAAGGACCCCACGAAGTGTTGGATATAAG
CCAGACTGTAA     *********                ************************************       *****

HPRT-wt Donor   TGCCCTGTAGTCTCTCTGTATGTTATATGTCACATTTTGTAATTAACAGCTTGCTGGTGAAAAGGACCCCACGAAGTGTTG
GATATAAGCCAGACTGTAA
**************** gRNA4-hr
HPRT-hr         GTGAATTACTTTTTTGTCAATCATTTAACCATCTTTAACCTAAAAGAGTTTATGTGAAATGGCTTATAATTGC-------GAGAGG
CAC

HPRT Edited     GTGAATTACTTTTTTGTCAATCATTTAACCATCTTTAACCTAAAAGAGTTTATGTGAAATGGCTTATAATTGCTTAGAGAATAT
TTGTAGAGAGGCAC  *********************************************************************

HPRT-wt Donor   GTGAATTACTTTTTTGTCAATCATTTAACCATCTTTAACCTAAAAGAGTTTATGTGAAATGGCTTATAATTGCTTAGAGAA
TATTTGTAGAGAGGCAC
**********
```

Step 3 co-targeting of Trex1 (+6-TG)

c.

Step 4 co-targeting of AAVS1 (+HAT)

HPRT-wt
gRNA3&4-hr
AAVS1gRNAt2     No DNA

SEQUENCE LISTING

```
<160> NUMBER OF SEQ ID NOS: 37

<210> SEQ ID NO 1
<211> LENGTH: 19
<212> TYPE: DNA
<213> ORGANISM: artificial sequence
<220> FEATURE:
<223> OTHER INFORMATION: HPRTg3 primer

<400> SEQUENCE: 1
aacatacaga gagactaca                                              19

<210> SEQ ID NO 2
<211> LENGTH: 19
<212> TYPE: DNA
<213> ORGANISM: artificial sequence
<220> FEATURE:
<223> OTHER INFORMATION: HPRTg4 primer

<400> SEQUENCE: 2
ttagagaata tttgtagag                                              19

<210> SEQ ID NO 3
<211> LENGTH: 19
<212> TYPE: DNA
<213> ORGANISM: artificial sequence
<220> FEATURE:
<223> OTHER INFORMATION: HPRTg3-hr primer

<400> SEQUENCE: 3
acaaaatgtg acatataca                                              19

<210> SEQ ID NO 4
<211> LENGTH: 19
<212> TYPE: DNA
<213> ORGANISM: artificial sequence
<220> FEATURE:
<223> OTHER INFORMATION: HPRTg4-hr primer

<400> SEQUENCE: 4
aatggcttat aattgcgag                                              19

<210> SEQ ID NO 5
<211> LENGTH: 20
<212> TYPE: DNA
<213> ORGANISM: artificial sequence
<220> FEATURE:
<223> OTHER INFORMATION: HPRT primer

<400> SEQUENCE: 5
tgggcaacag agcgagattc                                             20
```

-continued

<210> SEQ ID NO 6
<211> LENGTH: 20
<212> TYPE: DNA
<213> ORGANISM: artificial sequence
<220> FEATURE:
<223> OTHER INFORMATION: HPRT primer

<400> SEQUENCE: 6
atcaaagtgg gaggccagtg                                               20

<210> SEQ ID NO 7
<211> LENGTH: 20
<212> TYPE: DNA
<213> ORGANISM: artificial sequence
<220> FEATURE:
<223> OTHER INFORMATION: Exo1 primer

<400> SEQUENCE: 7
tccagttcca gctgcctaga                                               20

<210> SEQ ID NO 8
<211> LENGTH: 20
<212> TYPE: DNA
<213> ORGANISM: artificial sequence
<220> FEATURE:
<223> OTHER INFORMATION: Exo1 primer

<400> SEQUENCE: 8
gtctgcacat tcctagccga                                               20

<210> SEQ ID NO 9
<211> LENGTH: 20
<212> TYPE: DNA
<213> ORGANISM: artificial sequence
<220> FEATURE:
<223> OTHER INFORMATION: AAVS1 primer

<400> SEQUENCE: 9
acaggaggtg ggggttagac                                               20

<210> SEQ ID NO 10
<211> LENGTH: 20
<212> TYPE: DNA
<213> ORGANISM: artificial sequence
<220> FEATURE:
<223> OTHER INFORMATION: AAVS1 primer

<400> SEQUENCE: 10
tatattccca gggccggtta                                               20

<210> SEQ ID NO 11
<211> LENGTH: 20
<212> TYPE: DNA
<213> ORGANISM: artificial sequence
<220> FEATURE:
<223> OTHER INFORMATION: Trex1 primer

<400> SEQUENCE: 11
gcagaccctc atcttttttcg                                              20

<210> SEQ ID NO 12
<211> LENGTH: 20
<212> TYPE: DNA
<213> ORGANISM: artificial sequence
<220> FEATURE:
<223> OTHER INFORMATION: HPRT primer -continued

<400> SEQUENCE: 12
gatgctcacc tctcccacac                    20

<210> SEQ ID NO 13
<211> LENGTH: 20
<212> TYPE: DNA
<213> ORGANISM: artificial sequence
<220> FEATURE:
<223> OTHER INFORMATION: HPRT primer

<400> SEQUENCE: 13
acatccatgg gacttctgcc                    20

<210> SEQ ID NO 14
<211> LENGTH: 20
<212> TYPE: DNA
<213> ORGANISM: artificial sequence
<220> FEATURE:
<223> OTHER INFORMATION: AAVS1 primer

<400> SEQUENCE: 14
acaggaggtg ggggttagac                    20

<210> SEQ ID NO 15
<211> LENGTH: 20
<212> TYPE: DNA
<213> ORGANISM: artificial sequence
<220> FEATURE:
<223> OTHER INFORMATION: AAVS1 primer

<400> SEQUENCE: 15
tatattccca gggccggtta                    20

<210> SEQ ID NO 16
<211> LENGTH: 20
<212> TYPE: DNA
<213> ORGANISM: artificial sequence
<220> FEATURE:
<223> OTHER INFORMATION: Trex1 primer

<400> SEQUENCE: 16
gcagaccctc atcttttcg                     20

<210> SEQ ID NO 17
<211> LENGTH: 21
<212> TYPE: DNA
<213> ORGANISM: artificial sequence
<220> FEATURE:
<223> OTHER INFORMATION: Trex1 primer

<400> SEQUENCE: 17
tactgggctc agatagttga c                  21

<210> SEQ ID NO 18
<211> LENGTH: 20
<212> TYPE: DNA
<213> ORGANISM: artificial sequence
<220> FEATURE:
<223> OTHER INFORMATION: Exo1 primer

<400> SEQUENCE: 18
tccagttcca gctgcctaga                    20

<210> SEQ ID NO 19
<211> LENGTH: 20

```
<212> TYPE: DNA
<213> ORGANISM: artificial sequence
<220> FEATURE:
<223> OTHER INFORMATION: Exo1 primer

<400> SEQUENCE: 19
gtctgcacat tcctagccga                                              20

<210> SEQ ID NO 20
<211> LENGTH: 3685
<212> TYPE: DNA
<213> ORGANISM: homo sapien

<400> SEQUENCE: 20
aaattgtaag cgttaatatt ttgttaaaat tcgcgttaaa ttttttgttaa atcagctcat    60 ttttttaacca ataggccgaa atcggcaaaa tcccttataa atcaaaagaa tagaccgaga   120
tagggttgag tgttgttcca gtttggaaca agagtccact attaaagaac gtggactcca   180
acgtcaaagg gcgaaaaacc gtctatcagg gcgatggccc actacgtgaa ccatcaccct   240
aatcaagttt tttggggtcg aggtgccgta aagcactaaa tcggaaccct aaagggagcc   300
cccgatttag agcttgacgg ggaaagccgg cgaacgtggc gagaaaggaa gggaagaaag   360
cgaaaggagc gggcgctagg gcgctggcaa gtgtagcggt cacgctgcgc gtaaccacca   420
cacccgccgc gcttaatgcg ccgctacagg gcgcgtcagg tggcactttt cggggaaatg   480
tgcgcggaac ccctatttgt ttatttttct aaatacattc aaatatgtat ccgctcatga   540
gacaataacc ctgataaatg cttcaataat attgaaaaag gaagagtcct gaggcggaaa   600
gaaccagctg tggaatgtgt gtcagttagg gtgtggaaag tccccaggct ccccagcagg   660
cagaagtatg caaagcatgc atctcaatta gtcagcaacc aggtgtggaa agtccccagg   720
ctccccagca ggcagaagta tgcaaagcat gcatctcaat tagtcagcaa ccatagtccc   780
gcccctaact ccgcccatcc cgcccctaac tccgcccagt tccgcccatt ctccgcccca   840
tggctgacta atttttttta tttatgcaga ggccgaggcc gcctcggcct ctgagctatt   900
ccagaagtag tgaggaggct ttttggagg cctaggcttt tgcaaagatc gatcaagaga   960
caggatgagg atcgtttcgc atgattgaac aagatggatt gcacgcaggt tctccggccg  1020
cttgggtgga gaggctattc ggctatgact gggcacaaca gacaatcggc tgctctgatg  1080
ccgccgtgtt ccggctgtca gcgcaggggc gcccggttct ttttgtcaag accgacctgt  1140
ccggtgccct gaatgaactg caagacgagg cagcgcggct atcgtggctg gccacgacgg  1200
gcgttccttg cgcagctgtg ctcgacgttg tcactgaagc gggaagggac tggctgctat  1260
tgggcgaagt gccggggcag gatctcctgt catctcacct tgctcctgcc gagaaagtat  1320
ccatcatggc tgatgcaatg cggcggctgc atacgcttga tccggctacc tgcccattcg  1380
accaccaagc gaaacatcgc atcgagcgag cacgtactcg gatggaagcc ggtcttgtcg  1440
atcaggatga tctggacgag gaacatcagg ggctcgcgcc agccgaactg ttcgccaggc  1500
tcaaggcgag catgcccgac ggcgaggatc tcgtcgtgac ccatggcgat gcctgcttgc  1560
cgaatatcat ggtggaaaat ggccgctttt ctggattcat cgactgtggc cggctgggtg  1620
tggcggaccg ctatcaggac atagcgttgg ctacccgtga tattgctgag gaacttggcg  1680
gcgaatgggc tgaccgcttc ctcgtgcttt acggtatcgc cgctcccgat tcgcagcgca  1740
tcgccttcta tcgccttctt gacgagttct tctgagcggg actctggggt tcgaaatgac  1800
cgaccaagcg acgcccaacc tgccatcacg agatttcgat tccaccgccg ccttctatga  1860
```

```
aaggttgggc ttcggaatcg ttttccggga cgccggctgg atgatcctcc agcgcgggga    1920
tctcatgctg gagttcttcg cccaccctag ggggaggcta actgaaacac ggaaggagac    1980
aataccggaa ggaacccgcg ctatgacggc aataaaaaga cagaataaaa cgcacggtgt    2040
tgggtcgttt gttcataaac gcggggttcg gtcccagggc tggcactctg tcgatacccc    2100
accgagaccc cattggggcc aatacgcccg cgtttcttcc ttttcccac ccacccccc     2160 aagttcgggt gaaggcccag ggctcgcagc aacgtcggg gcggcaggcc ctgccatagc    2220
ctcaggttac tcatatatac tttagattga tttaaaactt cattttaat ttaaaggat    2280 ctaggtgaag atccttttg ataatctcat gaccaaaatc ccttaacgtg agttttcgtt    2340
ccactgagcg tcagaccccg tagaaaagat caaaggatct tcttgagatc cttttttct    2400 gcgcgtaatc tgctgcttgc aaacaaaaaa accaccgcta ccagcggtgg tttgtttgcc    2460
ggatcaagag ctaccaactc tttttccgaa ggtaactggc ttcagcagag cgcagatacc    2520
aaatactgtc cttctagtgt agccgtagtt aggccaccac ttcaagaact ctgtagcacc    2580
gcctacatac ctcgctctgc taatcctgtt accagtggct gctgccagtg gcgataagtc    2640
gtgtcttacc gggttggact caagacgata gttaccggat aaggcgcagc ggtcgggctg    2700 aacgggggt tcgtgcacac agcccagctt ggagcgaacg acctacaccg aactgagata    2760
cctacagcgt gagctatgag aaagcgccac gcttcccgaa gggagaaagg cggacaggta    2820
tccggtaagc ggcagggtcg gaacaggaga gcgcacgagg gagcttccag ggggaaacgc    2880
ctggtatctt tatagtcctg tcgggtttcg ccacctctga cttgagcgtc gatttttgtg    2940
atgctcgtca ggggggcgga gcctatggaa aaacgccagc aacgcggcct ttttacggtt    3000
cctggccttt tgctggcctt tgctcacat gttgtgctag cattcgcgaa ttccattcag    3060
gctgcgcaac tgttgggaag ggcgatcggt gcgggcctct tcgctattac gccagctggc    3120
gaaaggggga tgtgctgcaa ggcgattaag ttgggtaacg ccagggtttt cccagtcacg    3180
acgttgtaaa acgacggcca gttagaacta gttgtacaaa aaagcaggct ttaaaggaac    3240
caattcagtc gactggatcc ggtaccaagg tcggcagga agagggccta tttcccatga    3300
ttccttcata tttgcatata cgatacaagg ctgttagaga gataattaga attaatttga    3360
ctgtaaacac aaagatatta gtacaaaata cgtgacgtag aaagtaataa tttcttgggt    3420
agtttgcagt tttaaaatta tgttttaaaa tggactatca tatgcttacc gtaacttgaa    3480
agtatttcga tttcttggct ttatatatct tgtggaaagg acgaaacacc gaagtaattc    3540
acttacagtc gttttagagc tagaaatagc aagttaaaat aaggctagtc cgttatcaac    3600
ttgaaaaagt ggcaccgagt cggtgctttt tttctagacc cagctttctt gtacaaagtt    3660
ggcattacaa ttggatatca cgcgt                                         3685
```

<210> SEQ ID NO 21
<211> LENGTH: 5126
<212> TYPE: DNA
<213> ORGANISM: homo sapien

<400> SEQUENCE: 21

```
aaattgtaag cgttaatatt ttgttaaaat tcgcgttaaa ttttgttaa atcagctcat      60 tttttaacca ataggccgaa atcggcaaaa tcccttataa atcaaaagaa tagaccgaga    120
tagggttgag tgttgttcca gtttggaaca agagtccact attaaagaac gtggactcca    180
acgtcaaagg gcgaaaaacc gtctatcagg gcgatggccc actacgtgaa ccatcaccct    240
aatcaagttt tttggggtcg aggtgccgta aagcactaaa tcggaaccct aaagggagcc    300
```

```
cccgatttag agcttgacgg ggaaagccgg cgaacgtggc gagaaaggaa gggaagaaag    360
cgaaaggagc gggcgctagg gcgctggcaa gtgtagcggt cacgctgcgc gtaaccacca    420
cacccgccgc gcttaatgcg ccgctacagg gcgcgtcagg tggcacttt cggggaaatg     480
tgcgcggaac ccctatttgt ttattttct aaatacattc aaatatgtat ccgctcatga     540
gacaataacc ctgataaatg cttcaataat attgaaaaag gaagagtcct gagcggaaag    600
aaccagctgt ggaatgtgtg tcagttaggg tgtggaaagt ccccaggctc ccagcaggc     660
agaagtatgc aaagcatgca tctcaattag tcagcaacca ggtgtggaaa gtccccaggc    720
tccccagcag gcagaagtat gcaaagcatg catctcaatt agtcagcaac catagtcccg    780
cccctaactc cgcccatccc gcccctaact ccgcccagtt ccgcccattc tccgcccat     840
ggctgactaa ttttttttat ttatgcagag gccgaggccg cctcggcctc tgagctattc    900
cagaagtagt gaggaggctt ttttggaggc ctaggctttt gcaaagatcg atcaagagac    960
aggatgagga tcgtttcgca tgattgaaca agatggattg cacgcaggtt ctccggccgc    1020
ttgggtggag aggctattcg gctatgactg ggcacaacag acaatcggct gctctgatgc    1080
cgccgtgttc cggctgtcag cgcaggggcg cccggttctt tttgtcaaga ccgacctgtc    1140
cggtgccctg aatgaactgc aagacgaggc agcgcggcta tcgtggctgg ccacgacggg    1200
cgttccttgc gcagctgtgc tcgacgttgt cactgaagcg ggaagggact ggctgctatt    1260
gggcgaagtg ccggggcagg atctcctgtc atctcacctt gctcctgccg agaaagtatc    1320
catcatggct gatgcaatgc ggcggctgca tacgcttgat ccggctacct gcccattcga    1380
ccaccaagcg aaacatcgca tcgagcgagc acgtactcgg atggaagccg gtcttgtcga    1440
tcaggatgat ctggacgagg aacatcaggg gctcgcgcca gccgaactgt tcgccaggct    1500
caaggcgagc atgcccgacg gcgaggatct cgtcgtgacc catggcgatg cctgcttgcc    1560
gaatatcatg gtggaaaatg gccgcttttc tggattcatc gactgtggcc ggctgggtgt    1620
ggcggaccgc tatcaggaca tagcgttggc tacccgtgat attgctgagg aacttggcgg    1680
cgaatgggct gaccgcttcc tcgtgcttta cggtatcgcc gctcccgatt cgcagcgcat    1740
cgccttctat cgccttcttg acgagttctt ctgagcggga ctctgggtt cgaaatgacc    1800
gaccaagcga cgcccaacct gccatcacga gatttcgatt ccaccgccgc cttctatgaa    1860
aggttgggct tcggaatcgt tttccgggac gccggctgga tgatcctcca gcgcgggat    1920
ctcatgctgg agttcttcgc ccaccctagg gggaggctaa ctgaaacacg aaggagaca    1980
ataccggaag gaacccgcgc tatgacggca ataaaaagac agaataaaac gcacggtgtt    2040
gggtcgtttg ttcataaacg cggggttcgg tcccagggct ggcactctgt cgataccccca   2100
ccgagaccca attggggcca atacgcccgc gtttcttcct tttccccacc caccccccca    2160
agttcgggtg aaggcccagg gctcgcagcc aacgtcgggg cggcaggccc tgccatagcc    2220
tcaggttact catatatact ttagattgat ttaaaacttc atttttaatt taaaaggatc    2280
taggtgaaga tccttttttga taatctcatg accaaaatcc cttaacgtga gttttcgttc    2340
cactgagcgt cagaccccgt agaaaagatc aaaggatctt cttgagatcc ttttttctg     2400
cgcgtaatct gctgcttgca acaaaaaaaa ccaccgctac cagcggtggt ttgtttgccg    2460
gatcaagagc taccaactct ttttccgaag gtaactggct tcagcagagc gcagatacca    2520
aatactgtcc ttctagtgta gccgtagtta ggccaccact tcaagaactc tgtagcaccg    2580
cctacatacc tcgctctgct aatcctgtta ccagtggctg ctgccagtgg cgataagtcg    2640
```

-continued

```
tgtcttaccg ggttggactc aagacgatag ttaccggata aggcgcagcg gtcgggctga    2700 acgggggtt cgtgcacaca gcccagcttg gagcgaacga cctacaccga actgagatac    2760
ctacagcgtg agctatgaga aagcgccacg cttcccgaag ggagaaaggc ggacaggtat    2820
ccggtaagcg gcagggtcgg aacaggagag cgcacgaggg agcttccagg gggaaacgcc    2880
tggtatcttt atagtcctgt cgggtttcgc cacctctgac ttgagcgtcg attttgtga    2940 tgctcgtcag gggggcggag cctatggaaa aacgccagca acgcggcctt tttacggttc    3000
ctggcctttt gctggccttt tgctcacatg ttgtgctagt tgtacaaaaa agcaggcttt    3060
aaaggaacca attcagtcga ctggatccgg taccaaggtc gggcaggaag agggcctatt    3120
tcccatgatt ccttcatatt tgcatatacg atacaaggct gttagagaga taattagaat    3180
taatttgact gtaaacacaa agatattagt acaaaatacg tgacgtagaa agtaataatt    3240
tcttgggtag tttgcagttt taaaattatg ttttaaaatg gactatcata tgcttaccgt    3300
aacttgaaag tatttcgatt tcttggcttt atatatcttg tggaaaggac gaaacaccga    3360
acatacagag agactacagt tttagagcta gaaatagcaa gttaaaataa ggctagtccg    3420
ttatcaactt gaaaaagtgg caccgagtcg gtgcttttt tctagaccca gctttcttgt    3480
acaaagttgg cattacaatt ccattcaggc tgcgcaactg ttgggaaggg cgatcggtgc    3540
gggcctcttc gctattacgc cagctggcga aggggggatg tgctgcaagg cgattaagtt    3600
gggtaacgcc agggttttcc cagtcacgac gttgtaaaac gacggccagt tagaactagt    3660
tgtacaaaaa agcaggcttt aaaggaacca attcagtcga ctggatccgg taccaaggtc    3720
gggcaggaag agggcctatt tcccatgatt ccttcatatt tgcatatacg atacaaggct    3780
gttagagaga taattagaat taatttgact gtaaacacaa agatattagt acaaaatacg    3840
tgacgtagaa agtaataatt tcttgggtag tttgcagttt taaaattatg ttttaaaatg    3900
gactatcata tgcttaccgt aacttgaaag tatttcgatt tcttggcttt atatatcttg    3960
tggaaaggac gaaacaccgt tagagaatat ttgtagaggt tttagagcta gaaatagcaa    4020
gttaaaataa ggctagtccg ttatcaactt gaaaaagtgg caccgagtcg gtgcttttt    4080 tctagaccca gctttcttgt acaaagttgg cattacaatt ggataattcg agctcggtac    4140
ccacatttat catctgaaat aataatgcaa caattattgt atattaaagc tgttcaacta    4200
tttcagccaa caagaagtgt caccctagcc tggccaggtt ccagttctaa ggacgtctgt    4260
actagactac agctttatgt gactaatggg aaccatcagt ctgttcaaat tatgaggtgc    4320
tggaaggaga aaacaattct cttttcctaaa ttttttatgcg tgttttgaaa aatgagtgag    4380 aaaagaagc aattacttac attcaaatcc ctgaagtatt cattatagtc aagggcatat    4440
cctacaacaa acttgtctgg aatttcaaat ccaacaacta aaaagaatca taattcatca    4500
tttagataaa gaaaacatca cttttaaatc taatactggc aaatgtgcct ctcgcaatta    4560
taagccattt cacataaaac tcttttaggt taaagatggt taaatgattg acaaaaaaag    4620
taattcactt acagtctggc ttatatccaa cagaccgcgg ggtcctttc accagcaagc    4680 tgttaattac aaaatgtgac atatacaggg cattacaaaa gagaagactg acgtttctaa    4740
acactgtttc atttcatccg tgctgagtgt accatggtca cttttaacac acccaaggaa    4800
agactatgaa atggagagct aaattatggg gattactagg aaggggcagc aatgagttga    4860
cactacagac aaggcacttg gttgatcacc tggaacctga aggacagttc tgagacctgc    4920
accctgacta cccatgtgtc cattgaaggg gagctaataa ggaggattaa tgggtacaga    4980
gtgtcaatga gcaaagatga aaagggctct cagtctagaa accttggaaa tacaatccct    5040
```

```
aaactataaa agggtgtggg agaggtgagc atcaccttt  atcacaacag ggacctgcag    5100
ccatgcatgc catggccacc acgcgt                                         5126

<210> SEQ ID NO 22
<211> LENGTH: 5247
<212> TYPE: DNA
<213> ORGANISM: homo sapien

<400> SEQUENCE: 22
aaattgtaag cgttaatatt ttgttaaaat tcgcgttaaa ttttgttaa atcagctcat       60 ttttaacca ataggccgaa atcggcaaaa tcccttataa atcaaaagaa tagaccgaga      120
tagggttgag tgttgttcca gtttggaaca agagtccact attaaagaac gtggactcca    180
acgtcaaagg gcgaaaaacc gtctatcagg gcgatggccc actacgtgaa ccatcaccct    240
aatcaagttt tttggggtcg aggtgccgta aagcactaaa tcggaaccct aaagggagcc    300
cccgatttag agcttgacgg ggaaagccgg cgaacgtggc gagaaaggaa gggaagaaag    360
cgaaaggagc gggcgctagg gcgctggcaa gtgtagcggt cacgctgcgc gtaaccacca    420
cacccgccgc gcttaatgcg ccgctacagg gcgcgtcagg tggcactttt cggggaaatg    480
tgcgcggaac ccctatttgt ttatttttct aaatacattc aaatatgtat ccgctcatga    540
gacaataacc ctgataaatg cttcaataat attgaaaaag gaagagtcct gaggcggaaa    600
gaaccagctg tggaatgtgt gtcagttagg gtgtggaaag tccccaggct ccccagcagg    660
cagaagtatg caaagcatgc atctcaatta gtcagcaacc aggtgtggaa agtccccagg    720
ctccccagca ggcagaagta tgcaaagcat gcatctcaat tagtcagcaa ccatagtccc    780
gcccctaact ccgcccatcc cgcccctaac tccgcccagt tccgcccatt ctccgcccca    840
tggctgacta attttttta tttatgcaga ggccgaggcc gcctcggcct ctgagctatt    900
ccagaagtag tgaggaggct ttttggagg cctaggcttt tgcaaagatc gatcaagaga    960
caggatgagg atcgtttcgc atgattgaac aagatggatt gcacgcaggt tctccggccg   1020
cttgggtgga gaggctattc ggctatgact gggcacaaca gacaatcggc tgctctgatg   1080
ccgccgtgtt ccggctgtca gcgcaggggc gcccggttct ttttgtcaag accgacctgt   1140
ccggtgccct gaatgaactg caagacgagg cagcgcggct atcgtggctg gccacgacgg   1200
gcgttccttg cgcagctgtg ctcgacgttg tcactgaagc gggaagggac tggctgctat   1260
tgggcgaagt gccggggcag gatctcctgt catctcacct tgctcctgcc gagaaagtat   1320
ccatcatggc tgatgcaatg cggcggctgc atacgcttga tccggctacc tgcccattcg   1380
accaccaagc gaaacatcgc atcgagcgag cacgtactcg gatggaagcc ggtcttgtcg   1440
atcaggatga tctggacgag gaacatcagg ggctcgcgcc agccgaactg ttcgccaggc   1500
tcaaggcgag catgcccgac ggcgaggatc tcgtcgtgac ccatggcgat gcctgcttgc   1560
cgaatatcat ggtggaaaat ggccgctttt ctggattcat cgactgtggc cggctgggtg   1620
tggcggaccg ctatcaggac atagcgttgg ctacccgtga tattgctgag aacttggcg    1680 gcgaatgggc tgaccgcttc ctcgtgcttt acggtatcgc cgctcccgat tcgcagcgca   1740
tcgccttcta tcgccttctt gacgagttct tctgagcggg actctgggt tcgaaatgac    1800 cgaccaagcg acgcccaacc tgccatcacg agatttcgat tccaccgccg ccttctatga   1860
aaggttgggc ttcggaatcg ttttccggga cgccggctgg atgatcctcc agcgcgggga   1920
tctcatgctg gagttcttcg cccacccctag ggggaggcta actgaaacac ggaaggagac   1980
```

```
aataccggaa ggaacccgcg ctatgacggc aataaaaaga cagaataaaa cgcacggtgt    2040
tgggtcgttt gttcataaac gcggggttcg gtcccagggc tggcactctg tcgatacccc    2100
accgagaccc cattggggcc aatacgcccg cgtttcttcc ttttcccac cccaccccc     2160 aagttcgggt gaaggcccag ggctcgcagc caacgtcggg gcggcaggcc ctgccatagc    2220
ctcaggttac tcatatatac tttagattga tttaaaactt catttttaat ttaaaggat    2280 ctaggtgaag atccttttg ataatctcat gaccaaaatc ccttaacgtg agttttcgtt    2340
ccactgagcg tcagaccccg tagaaaagat caaaggatct tcttgagatc cttttttct    2400 gcgcgtaatc tgctgcttgc aaacaaaaaa accaccgcta ccagcggtgg tttgtttgcc    2460
ggatcaagag ctaccaactc ttttccgaa ggtaactggc ttcagcagag cgcagatacc    2520
aaatactgtc cttctagtgt agccgtagtt aggccaccac ttcaagaact ctgtagcacc    2580
gcctacatac ctcgctctgc taatcctgtt accagtggct gctgccagtg gcgataagtc    2640
gtgtcttacc gggttggact caagacgata gttaccggat aaggcgcagc ggtcgggctg    2700
aacggggggt tcgtgcacac agcccagctt ggagcgaacg acctacaccg aactgagata    2760
cctacagcgt gagctatgag aaagcgccac gcttcccgaa gggagaaagg cggacaggta    2820
tccggtaagc ggcagggtcg gaacaggaga gcgcacgagg gagcttccag ggggaaacgc    2880
ctggtatctt tatagtcctg tcgggtttcg ccacctctga cttgagcgtc gatttttgtg    2940
atgctcgtca ggggggcgga gcctatggaa aaacgccagc aacgcggcct ttttacggtt    3000
cctggccttt tgctggcctt ttgctcacat gttgtgctag ttgtacaaaa aagcaggctt    3060
taaaggaacc aattcagtcg actggatccg gtaccaaggt cgggcaggaa gagggcctat    3120
ttcccatgat tccttcatat ttgcatatac gatacaaggc tgttagagag ataattagaa    3180
ttaatttgac tgtaaacaca aagatattag tacaaaatac gtgacgtaga aagtaataat    3240
ttcttgggta gtttgcagtt ttaaaattat gttttaaaat ggactatcat atgcttaccg    3300
taacttgaaa gtatttcgat ttcttggctt tatatatctt gtggaaagga cgaaacaccg    3360
acaaaatgtg acatatacag ttttagagct agaaatagca agttaaaata aggctagtcc    3420
gttatcaact tgaaaagtg gcaccgagtc ggtgcttttt ttctagaccc agctttcttg    3480
tacaaagttg gcattacaat tccattcagg ctgcgcaact gttgggaagg gcgatcggtg    3540
cgggcctctt cgctattacg ccagctggcg aaagggggat gtgctgcaag gcgattaagt    3600
tgggtaacgc cagggttttc ccagtcacga cgttgtaaaa cgacggccag ttagaactag    3660
ttgtacaaaa aagcaggctt taaaggaacc aattcagtcg actggatccg gtaccaaggt    3720
cgggcaggaa gagggcctat ttcccatgat tccttcatat ttgcatatac gatacaaggc    3780
tgttagagag ataattagaa ttaatttgac tgtaaacaca aagatattag tacaaaatac    3840
gtgacgtaga aagtaataat ttcttgggta gtttgcagtt ttaaaattat gttttaaaat    3900
ggactatcat atgcttaccg taacttgaaa gtatttcgat ttcttggctt tatatatctt    3960
gtggaaagga cgaaacaccg aatggcttat aattgcgagg ttttagagct agaaatagca    4020
agttaaaata aggctagtcc gttatcaact tgaaaaagtg gcaccgagtc ggtgcttttt    4080
ttctagaccc agctttcttg tacaaagttg gcattacaat tcgagctcgg tacccgggga    4140
tcctctagag tcgatgctca cctctcccac acccttttat agtttaggga ttgtatttcc    4200
aaggtttcta gactgagagc ccttttcatc tttgctcatt gacactctgt acccattaat    4260
cctccttatt agctccccct caatggacac atgggtagtc agggtgcagg tctcagaact    4320
gtccttcagg ttcaggtgta tcaaccaagt gccttgtctg tagtgtcaac tcattgctgc    4380
```

-continued

```
ccettcctag taatccccat aatttagctc tccatttcat agtctttcct tgggtgtgtt    4440
aaaagtgacc atggtacact cagcacggat gaaatgaaac agtgtttaga aacgtcagtc    4500
ttctcttttg taatgccctg tagtctctct gtatgttata tgtcacattt tgtaattaac    4560
agcttgctgg tgaaaggac cccacgaagt gttggatata agccagactg taagtgaatt     4620
actttttttg tcaatcattt aaccatcttt aacctaaaag agttttatgt gaaatggctt    4680
ataattgctt agagaatatt tgtagagagg cacatttgcc agtattagat ttaaaagtga    4740
tgttttcttt atctaaatga tgaattatga ttcttttttag ttgttggatt tgaaattcca   4800
gacaagtttg ttgtaggata tgcccttgac tataatgaat acttcaggga tttgaatgta    4860
agtaattgct tcttttttctc actcattttt caaaacacgc ataaaaattt aggaaagaga   4920
attgttttct ccttccagca cctcataatt tgaacagact gatggttccc attagtcaca    4980
taaagctgta gtctagtaca gacgtcctta gaactggaac ctggccaggc tagggtgaca    5040
cttcttgttg gctgaaatag ttgaacagct ttaatataca ataattgttg cattattatt   5100
tcagatgata aatgtggtca taagtaagaa ataaatgatc gagtttagtc ttttaattca    5160
ctgtcctttg aatacctgcc tcttactctg gaggcagaag tcccatggat gtgacctgca    5220
gccatgcatg ccatggccac cacgcgt                                        5247
```

<210> SEQ ID NO 23
<211> LENGTH: 956
<212> TYPE: DNA
<213> ORGANISM: homo sapien

<400> SEQUENCE: 23

```
ggtacccaca tttatcatct gaaataataa tgcaacaatt attgtatatt aaagctgttc     60
aactatttca gccaacaaga agtgtcaccc tagcctggcc aggttccagt tctaaggacg    120
tctgtactag actacagctt tatgtgacta atgggaacca tcagtctgtt caaattatga    180
ggtgctggaa ggagaaaaca attctctttc ctaaattttt atgcgtgttt tgaaaaatga    240
gtgagaaaaa gaagcaatta cttacattca aatccctgaa gtattcatta tagtcaaggg    300
catatcctac aacaaacttg tctggaattt caaatccaac aactaaaaag aatcataatt    360
catcatttag ataaagaaaa catcactttt aaatctaata ctggcaaatg tgcctctcgc    420
aattataagc catttcacat aaaactcttt taggttaaag atggttaaat gattgacaaa    480
aaaagtaatt cacttacagt ctggcttata tccaacagac cgcggggtcc ttttcaccag    540
caagctgtta attacaaaat gtgacatata cagggcatta caaagagaa gactgacgtt     600 tctaaacact gtttcatttc atccgtgctg agtgtaccat ggtcactttt aacacaccca    660
aggaaagact atgaaatgga gagctaaatt atggggatta ctaggaaggg gcagcaatga    720
gttgacacta cagacaaggc acttggttga tcacctggaa cctgaaggac agttctgaga    780
cctgcaccct gactacccat gtgtccattg aaggggagct aataaggagg attaatgggt    840
acagagtgtc aatgagcaaa gatgaaaagg gctctcagtc tagaaaacctt ggaaatacaa    900 tccctaaact ataaaagggt gtgggagagg tgagcatcac cttttatcac aacagg         956
```

<210> SEQ ID NO 24
<211> LENGTH: 1060
<212> TYPE: DNA
<213> ORGANISM: homo sapien

<400> SEQUENCE: 24

```
gatgctcacc tctcccacac cctttttatag tttagggatt gtatttccaa ggtttctaga      60
ctgagagccc ttttcatctt tgctcattga cactctgtac ccattaatcc tccttattag     120
ctccccttca atggacacat gggtagtcag ggtgcaggtc tcagaactgt ccttcaggtt     180
ccaggtgatc aaccaagtgc cttgtctgta gtgtcaactc attgctgccc cttcctagta     240
atccccataa tttagctctc catttcatag tctttccttg ggtgtgttaa aagtgaccat     300
ggtacactca gcacggatga aatgaaacag tgtttagaaa cgtcagtctt ctcttttgta     360
atgccctgta gtctctctgt atgttatatg tcacattttg taattaacag cttgctggtg     420
aaaaggaccc cacgaagtgt tggatataag ccagactgta agtgaattac ttttttttgtc     480 aatcatttaa ccatctttaa cctaaaagag ttttatgtga aatggcttat aattgcttag     540
agaatatttg tagagaggca catttgccag tattagattt aaaagtgatg ttttctttat     600
ctaaatgatg aattatgatt cttttttagtt gttggatttg aaattccaga caagtttgtt     660
gtaggatatg cccttgacta taatgaatac ttcagggatt tgaatgtaag taattgcttc     720
tttttctcac tcatttttca aaacacgcat aaaaatttag gaaagagaat tgttttctcc     780
ttccagcacc tcataatttg aacagactga tggttcccat tagtcacata aagctgtagt     840
ctagtacaga cgtccttaga actggaacct ggccaggcta gggtgacact tcttgttggc     900
tgaaatagtt gaacagcttt aatatacaat aattgttgca ttattatttc agatgataaa     960
tgtggtcata agtaagaaat aaatgatcga gtttagtctt ttaattcact gtcctttgaa    1020
tacctgcctc ttactctgga ggcagaagtc ccatggatgt                          1060
```

<210> SEQ ID NO 25
<211> LENGTH: 19
<212> TYPE: DNA
<213> ORGANISM: homo sapien

<400> SEQUENCE: 25

```
aagtaattca cttacagtc                                                    19
```

<210> SEQ ID NO 26
<211> LENGTH: 100
<212> TYPE: DNA
<213> ORGANISM: artificial sequence
<220> FEATURE:
<223> OTHER INFORMATION: HPRT-wt

<400> SEQUENCE: 26

```
tgccctgtag tctctctgta tgttatatgt cacattttgt aattaacagc ttgctggtga      60 aaaggaccccc acgaagtgtt ggatataagc cagactgtaa                          100
```

<210> SEQ ID NO 27
<211> LENGTH: 84
<212> TYPE: DNA
<213> ORGANISM: artificial sequence
<220> FEATURE:
<223> OTHER INFORMATION: HPRT-Edited

<400> SEQUENCE: 27

```
tgccctgtat atgtcacatt ttgtaattaa cagcttgctg gtgaaaagga ccccgcggtc      60
tgttggatat aagccagact gtaa                                             84
```

<210> SEQ ID NO 28
<211> LENGTH: 84
<212> TYPE: DNA
<213> ORGANISM: artificial sequence

```
<220> FEATURE:
<223> OTHER INFORMATION: HPRT-hr Donor

<400> SEQUENCE: 28
tgccctgtat atgtcacatt ttgtaattaa cagcttgctg gtgaaaagga ccccgcggtc    60
tgttggatat aagccagact gtaa                                          84

<210> SEQ ID NO 29
<211> LENGTH: 100
<212> TYPE: DNA
<213> ORGANISM: artificial sequence
<220> FEATURE:
<223> OTHER INFORMATION: HPRT-wt

<400> SEQUENCE: 29
gtgaattact tttttgtca atcatttaac catctttaac ctaaaagagt tttatgtgaa     60
atggcttata attgcttaga gaatatttgt agagaggcac                        100

<210> SEQ ID NO 30
<211> LENGTH: 84
<212> TYPE: DNA
<213> ORGANISM: artificial sequence
<220> FEATURE:
<223> OTHER INFORMATION: HPRT Edited

<400> SEQUENCE: 30
gtgaattact tttttgtca atcatttaac catctttaac ctaaaagagt tttatgtgaa     60
atggcttata attgcgagag gcac                                          84

<210> SEQ ID NO 31
<211> LENGTH: 84
<212> TYPE: DNA
<213> ORGANISM: artificial sequence
<220> FEATURE:
<223> OTHER INFORMATION: HPRT-hr Donor

<400> SEQUENCE: 31
gtgaattact tttttgtca atcatttaac catctttaac ctaaaagagt tttatgtgaa     60
atggcttata attgcgagag gcac                                          84

<210> SEQ ID NO 32
<211> LENGTH: 84
<212> TYPE: DNA
<213> ORGANISM: artificial sequence
<220> FEATURE:
<223> OTHER INFORMATION: HPRT-hr

<400> SEQUENCE: 32
tgccctgtat atgtcacatt ttgtaattaa cagcttgctg gtgaaaagga ccccgcggtc    60
tgttggatat aagccagact gtaa                                          84

<210> SEQ ID NO 33
<211> LENGTH: 100
<212> TYPE: DNA
<213> ORGANISM: artificial sequence
<220> FEATURE:
<223> OTHER INFORMATION: HPRT Edited

<400> SEQUENCE: 33
tgccctgtag tctctctgta tgttatatgt cacattttgt aattaacagc ttgctggtga    60
aaaggacccc acgaagtgtt ggatataagc cagactgtaa                        100
```

```
<210> SEQ ID NO 34
<211> LENGTH: 100
<212> TYPE: DNA
<213> ORGANISM: artificial sequence
<220> FEATURE:
<223> OTHER INFORMATION: HPRT-wt Donor

<400> SEQUENCE: 34
tgccctgtag tctctctgta tgttatatgt cacattttgt aattaacagc ttgctggtga      60
aaaggacccc acgaagtgtt ggatataagc cagactgtaa                           100

<210> SEQ ID NO 35
<211> LENGTH: 84
<212> TYPE: DNA
<213> ORGANISM: artificial sequence
<220> FEATURE:
<223> OTHER INFORMATION: HPRT-hr

<400> SEQUENCE: 35
gtgaattact tttttgtca atcatttaac catctttaac ctaaaagagt tttatgtgaa       60
atggcttata attgcgagag gcac                                             84

<210> SEQ ID NO 36
<211> LENGTH: 100
<212> TYPE: DNA
<213> ORGANISM: artificial sequence
<220> FEATURE:
<223> OTHER INFORMATION: HPRT Edited

<400> SEQUENCE: 36
gtgaattact tttttgtca atcatttaac catctttaac ctaaaagagt tttatgtgaa       60
atggcttata attgcttaga gaatatttgt agagaggcac                           100

<210> SEQ ID NO 37
<211> LENGTH: 100
<212> TYPE: DNA
<213> ORGANISM: artificial sequence
<220> FEATURE:
<223> OTHER INFORMATION: HPRT-wt Donor

<400> SEQUENCE: 37
gtgaattact tttttgtca atcatttaac catctttaac ctaaaagagt tttatgtgaa       60
atggcttata attgcttaga gaatatttgt agagaggcac                           100
```

METHODS FOR ENRICHING GENE-TARGETED CELLS

CROSS-REFERENCE TO RELATED APPLICATIONS

This application claims priority to U.S. Application No. 62/405,540, filed Oct. 7, 2016, which is incorporated herein by reference in its entirety.

REFERENCE TO GOVERNMENT GRANTS

This invention was made with government support under Grant No. GM057962 awarded by the National Institutes of Health. The government has certain rights in the invention.

FIELD

The present disclosure relates generally to the field of gene targeting. More particularly, the present disclosure relates to methods for enriching cells in which a gene sequence has been targeted for alteration or for editing. Enrichment proceeds via co-targeting of hypoxanthine phosphoribosyltransferase (HPRT), followed by selection with hypoxanthineaminopterin-thymidine (HAT) or 6-thioguanine (6-TG).

BACKGROUND

The clustered regularly interspaced short palindromic repeats (CRISPR)-Cas9 system uses a 19-20 nucleotide (nt) guide RNA (gRNA) to direct the Cas9 endonuclease to introduce a DNA double-strand (ds) break (DSB) at practically any specified site in the genome. The DSB is usually repaired by non-homologous end joining (NHEJ), resulting in a small insertion or deletion (indel) that disrupts the target gene. If a homologous donor DNA is introduced into cells at the same time, the DSB can also be repaired by homology-dependent repair (HDR), leading to gene editing. The power of the CRISPR technology has made it possible to disrupt all of the predicted genes in the human genome, revealing that there are approximately 2000 core essential genes and many other context-dependent genes.

Despite the success of CRISPR, the efficiency is still highly variable due to multiple factors, such as guide RNA effectiveness, transfection efficiency, retrovirus titer, and cell type. This problem is compounded exponentially when one needs to target sequentially two or more genes (iterative gene targeting) to analyze their functional relationship. Various methods have thus been developed to enrich cells that have been successfully targeted. A common enrichment strategy is to use markers, such GFP, drug resistance, or death receptors to select for cells that have been transfected or infected. However, the expression of these markers does not necessarily correlate with high levels of Cas9 or gRNAs. Selection for drug resistance also leads to the integration of foreign DNA into the chromosome, which is itself an alteration to the genome and risks oncogenic transformation. For iterative gene targeting, if each round uses a separate drug resistance gene, one would quickly run out of choice and the genome would be littered with foreign DNA.

One alternative enrichment method uses co-targeting of the HPRT gene. This gene encodes an enzyme that catalyzes the conversion of hypoxanthine to inosinemonophosphate and guanine to guanosine monophosphate in the non-essential purine salvage pathway. HPRT-positive cells are sensitive to 6-TG, which is converted to the cytotoxic nucleotide form by HPRT. The strategy is to co-express Cas9 with two guide RNAs, one against HPRT and the other against the gene of interest. The resulting 6-TG resistant cells are highly enriched for mutations in the gene of interest with no other genetic imprints.

One unique feature of the HPRT gene is that it can be both selected and counterselected. HPRT mutant cells are resistant to 6-TG but sensitive to HAT. In HAT media, the de novo synthesis of nucleotides is blocked by aminopterin, a strong inhibitor of the key enzyme dihydrofolate reductase (DHFR). Cells have to rely on the exogenously provided hypoxanthine and thymidine to synthesize nucleotides via the HPRT-dependent salvage pathway. As such, only HPRT wild type cells can survive and proliferate after HAT selection.

SUMMARY

The present disclosure provides nucleic acids for editing or altering the HPRT gene in a cell. A nucleic acid may comprise the sequence of SEQ ID NO:23 or SEQ ID NO:24, or the complement thereof. A gRNA for altering or editing the HPRT gene may comprise the nucleic acid sequence of SEQ ID NO:1, SEQ ID NO:2, SEQ ID NO:3, SEQ ID NO:4, or SEQ ID NO:25, or the complement thereof. A vector comprising the nucleic acid sequence of SEQ ID NO:23 and a vector comprising the nucleic acid sequence of SEQ ID NO:24 are provided. The vector may comprise a plasmid. The plasmid may comprise the nucleic acid sequence of SEQ ID NO:21 or SEQ ID NO:22. A vector comprising a gRNA for altering or editing the HPRT gene is further provided. The vector may comprise a plasmid. The plasmid may comprise the nucleic acid sequence of EQ ID NO:20.

Any such nucleic acids, vectors, or plasmids may be comprised in a kit. A kit may comprise two or more nucleic acids, vectors, or plasmids. The kit may comprise two or more plasmids, including a plasmid comprising the nucleic acid sequence of SEQ ID NO:23 and a plasmid comprising the nucleic acid sequence of SEQ ID NO:24. The kit may comprise two or more plasmids, including a plasmid having the nucleic acid sequence of SEQ ID NO:20, a plasmid having the nucleic acid sequence of SEQ ID NO:21, and/or a plasmid having the nucleic acid sequence of SEQ ID NO:22. The kit may further comprise a plasmid encoding a gRNA for altering or editing the HPRT gene, including a plasmid comprising the nucleic acid sequence of SEQ ID NO:25.

The present disclosure also provides methods for altering the nucleic acid sequence of a target gene. In some embodiments, the methods may comprise transfecting a Cas-9 competent cell with a gRNA that hybridizes to a nucleic acid sequence of the hypoxanthine guanine phosphoribosyl transferase (HPRT) gene, thereby introducing an alteration to the HPRT gene, and then culturing the cell in a medium comprising 6-thioguanine. Alternately, the methods may comprise a) providing a Cas9-competent cell comprising a HPRT gene comprising an alteration. Then, with the cell comprising having an alteration in the HPRT being obtained or provided, the methods comprise b) co-transfecting the cell with a gRNA that hybridizes to a nucleic acid sequence of a target gene, a first gRNA that hybridizes to the HPRT gene upstream of the alteration, a second gRNA that hybridizes to the HPRT gene downstream of the alteration, and a first donor plasmid comprising a HPRT nucleic acid sequence that corrects the alteration and that lacks a sequence complementary to the sequence of first and second gRNA that hybridizes to the HPRT gene, and then culturing the cell in a medium comprising HA), c) transfecting the cell with a third gRNA that hybridizes to the HPRT gene, thereby re-introducing the alteration to the HPRT gene, and optionally with a gRNA that hybridizes to a nucleic acid sequence of a subsequent target gene, and then culturing the cell in a medium comprising 6-thioguanine, and d) co-transfecting the cell with a gRNA that hybridizes to a nucleic acid sequence of a subsequent target gene, a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT, or e) co-transfecting the cell with a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT.

The methods may further comprise repeating step c), and thereafter repeating steps b) through d) a plurality of times, and upon the last repeat, step e) is carried out instead of step d). During these repeats, the target gene in step b) is different each time step b) is repeated, and the subsequent target gene in step d) is both different from the target gene in step b) and is a different subsequent target gene each time step d) is repeated.

The Cas9-competent cell may comprise Cas9 integrated into its genome. The Cas9-competent cell may alternately be transfected with a plasmid encoding Cas9, which may optionally comprise an inducible promoter. The Cas-9 competent cell may be a primary isolate, and may be isolated from a non-human mammal or may be isolated from a human being.

The first donor plasmid may comprise the nucleic acid sequence of SEQ ID NO:21. The second donor plasmid may comprise the nucleic acid sequence of SEQ ID NO:22. The HPRT nucleic acid sequence that corrects the alteration and that lacks a sequence complementary to the sequence of first and second gRNA that hybridizes to the HPRT gene may comprise the nucleic acid sequence of SEQ ID NO:23. The wild type HPRT nucleic acid sequence may comprise the nucleic acid sequence of SEQ ID NO:24.

In some embodiments, the methods comprise a) co-transfecting a Cas9-competent cell with a gRNA that hybridizes to a nucleic acid sequence of a target gene and a first gRNA that hybridizes to a nucleic acid sequence of the HPRT gene, thereby introducing an alteration to the HPRT gene, and then culturing the cell in a medium comprising 6-thioguanine, b) co-transfecting the cell with a second gRNA that hybridizes to the HPRT gene upstream of the alteration, a third gRNA that hybridizes to the HPRT gene downstream of the alteration, and a first donor plasmid comprising a HPRT nucleic acid sequence that corrects the alteration but lacks a sequence complementary to the sequence of second and third gRNA, and, optionally, a gRNA that hybridizes to a nucleic acid sequence of a subsequent target gene, and then culturing the cell in a medium comprising HAT, c) co-transfecting the cell with the first gRNA, thereby re-introducing the alteration to the HPRT gene, and a gRNA that hybridizes to a nucleic acid sequence of a subsequent target gene, and then culturing the cell in a medium comprising 6-thioguanine, and d) co-transfecting the cell with a fourth gRNA that hybridizes to the HPRT gene upstream of the alteration, a fifth gRNA that hybridizes to the HPRT gene downstream of the alteration, and a second donor plasmid comprising a HPRT nucleic acid sequence comprising a wild type HPRT nucleic acid sequence that corrects the alteration, and optionally a gRNA that hybridizes to a nucleic acid sequence of a subsequent target gene, and then culturing the cell in a medium comprising HAT.

The methods may further comprise e) repeating step c), and thereafter repeating steps b) through d) a plurality of times, and, optionally, repeating step e) a plurality of additional times. During these repeats, the subsequent target gene in step c) is a different gene each time step c) is repeated, and each subsequent target gene in step c) is different from the target gene in step a).

The Cas9-competent cell may comprise Cas9 integrated into its genome. The Cas9-competent cell may alternately be transfected with a plasmid encoding Cas9, which may optionally comprise an inducible promoter. The Cas-9 competent cell may be a primary isolate, and may be isolated from a non-human mammal or may be isolated from a human being.

The first donor plasmid may comprise the nucleic acid sequence of SEQ ID NO:21. The second donor plasmid may comprise the nucleic acid sequence of SEQ ID NO:22. The HPRT nucleic acid sequence that corrects the alteration and that lacks a sequence complementary to the sequence of first and second gRNA that hybridizes to the HPRT gene may comprise the nucleic acid sequence of SEQ ID NO:23. The wild type HPRT nucleic acid sequence may comprise the nucleic acid sequence of SEQ ID NO:24.

In some embodiments, the methods comprise a) providing a Cas9-competent cell comprising a hypoxanthine guanine phosphoribosyl transferase (HPRT) gene comprising an alteration, b) co-transfecting the cell with a first gRNA that hybridizes upstream of a nucleic acid sequence of a target gene, a second gRNA that hybridizes downstream of the nucleic acid sequence of the target gene, a first donor plasmid comprising a nucleic acid sequence that alters the nucleic acid sequence of the target gene, a first gRNA that hybridizes to the HPRT gene upstream of the alteration, a second gRNA that hybridizes to the HPRT gene downstream of the alteration, and a first donor plasmid comprising a HPRT nucleic acid sequence that corrects the alteration and that lacks a sequence complementary to the sequence of first and second gRNA that hybridizes to the HPRT gene, and then culturing the cell in a medium comprising HAT, c) transfecting the cell with a third gRNA that hybridizes to the HPRT gene, thereby re-introducing the alteration to the HPRT gene, and then culturing the cell in a medium comprising 6-thioguanine; and d) co-transfecting the cell with a first gRNA that hybridizes upstream of a nucleic acid sequence of a subsequent target gene, a second gRNA that hybridizes downstream of the nucleic acid sequence of the subsequent target gene, and a first donor plasmid comprising a nucleic acid sequence that alters the nucleic acid sequence of the subsequent target gene, a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT; or e) co-transfecting the cell with a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT.

The methods may further comprise repeating step c), and thereafter repeating steps b) through d) a plurality of times. During the repeats, the target gene in step b) is a different gene each time step b) is repeated, and the subsequent target gene in step d) is both different from the target gene in step b) and is a different gene each time step d) is repeated.

The Cas9-competent cell may comprise Cas9 integrated into its genome. The Cas9-competent cell may alternately be transfected with a plasmid encoding Cas9, which may optionally comprise an inducible promoter. The Cas-9 competent cell may be a primary isolate, and may be isolated from a non-human mammal or may be isolated from a human being.

The first donor plasmid may comprise the nucleic acid sequence of SEQ ID NO:21. The second donor plasmid may comprise the nucleic acid sequence of SEQ ID NO:22. The HPRT nucleic acid sequence that corrects the alteration and that lacks a sequence complementary to the sequence of first and second gRNA that hybridizes to the HPRT gene may comprise the nucleic acid sequence of SEQ ID NO:23. The wild type HPRT nucleic acid sequence may comprise the nucleic acid sequence of SEQ ID NO:24.

In any of the methods where the cell is a primary isolate, following editing of the target gene and, where applicable, each subsequent target gene, the methods may further comprise administering the cell back to the non-human mammal or the human being from which it was isolated. Thus, the methods may comprise isolating a cell from a non-human mammal or a human being, making the cell Cas-9 competent, editing a target gene and, optionally also editing one or a plurality of subsequent target genes according to the methods described or exemplified herein, and then administering the cell back to the non-human mammal or the human being from which it was isolated.

BRIEF DESCRIPTION OF THE DRAWINGS

FIG. 1 (panel a) shows the design for the editing gRNAs and the donor sequence. The donor (HPRT-hr) lacks the target sequences for the two editing gRNAs and contains some silent mutations in exon 8. Wild type sequences and mutated sequences are shown. FIG. 1 (panel b) shows crystal violet staining of colonies formed after HAT selection of the transfected cells. The Cas9 gene was integrated in the genome and induced by doxycycline. The amount of each plasmid is: 0.3 µg for HPRT gRNA3, 0.3 µg for HPRT gRNA4, and 0.2 µg for the donor HPRT-hr. FIG. 1 (panel c) shows a sequence chromatogram of the exon 8 region disrupted by Cas9 and HPRT gRNA2 in pooled 6-TG resistant cells. Underlined are the sequences corresponding to the silent mutations and the gRNA2 target in the donor. FIG. 1 (panel d) shows a sequence chromatogram of the edited HPRT gene in the pooled HAT resistant cells. Underlined are the mutated targets of editing gRNAs 3 and 4, the silent mutations in exon 8, and the corrected target of gRNA2. FIG. 1 (panel e; SEQ ID NOs: 26, 27, 28, 29, 30, and 31 top to bottom) shows a sequence alignment of the wild type HPRT gene, the donor, and the corrected HPRT gene.

FIG. 2 (panel a) shows crystal violet staining of colonies formed after HAT selection of cells transfected with the indicated DNA. The amount of each plasmid is: 0.3 µg for HPRT gRNA3-gRNA4 (same plasmid), 0.3 µg for Exo1 or Trex1 gRNA, and 0.2 µg for the donor HPRT-hr. FIG. 2 (panel b) shows sequence chromatograms of the Exo1 target region and Trex1 target region in the pooled HAT resistant cells.

FIG. 3 (panel a) shows re-disruption of the corrected HPRT gene. Left: Crystal violet staining of colonies formed after 6-TG selection of the corrected cells transfected with HPRT gRNA2. Right: the sequence chromatogram of the HPRT target region in the pooled 6-TG resistant cells. Underlined are the mutated targets of editing gRNA3-hr and gRNA4-hr, the silent mutations in exon 8, and the mutated target of gRNA2. 0.8 µg for HPRT gRNA2 was used for transfection. FIG. 3 (panel b) shows re-correction of the re-disrupted HPRT gene. Left: Crystal violet staining of colonies formed after HAT selection of the re-disrupted cells transfected with new editing gRNAs and completely wild type HPRT donor. Right: the sequence chromatogram of the HPRT target region in the pooled HAT resistant cells. Underlined are the wild type targets of editing gRNA3 and gRNA4, the wild type signature in exon 8, and the wild type target of gRNA2. FIG. 3 (panel c; SEQ ID NOs: 32, 33, 34, 35, 36, and 37 top to bottom) shows a sequence alignment of the first HR-donor corrected HPRT gene, the re-corrected HPRT gene, and the wild type HPRT donor. The amount of each plasmid is: 0.4 µg for HPRT gRNA3-gRNA4, and 0.4 µg for the donor HPRT-wt.

FIG. 4 (panel a) shows a 4-step cycle of HPRT gene disruption and correction. FIG. 4 (panel b) shows co-targeting of Trex1 during step 3. Left: Crystal violet staining of colonies formed after 6-TG selection of the Exo1 mutant cells from step 2 co-targeting transfected with the Trex1 and HPRT gRNAs. Right: sequence chromatograms of the Trex1 target region in the pooled 6-TG resistant cells. The amount of each plasmid is: 0.4 µg for HPRT gRNA2 and 0.4 µg for Trex1 gRNA. FIG. 4 (panel c) shows co-targeting of AAVS1 during step 4. Left: Crystal violet staining of colonies formed after HAT selection of the Exo1/Trex1 mutant cells from step 3 co-targeting transfected with the AAVS1 and HPRT gRNAs. Right: sequence chromatograms of the AAVS1 target region in the pooled HAT resistant cells. The amount of each plasmid is: 0.4 µg for HPRT gRNA3-gRNA4 (same plasmid), 0.2 µg for AAVS1 gRNA, and 0.2 µg for the donor HPRT-wt.

DESCRIPTION OF EMBODIMENTS

Figure 1:
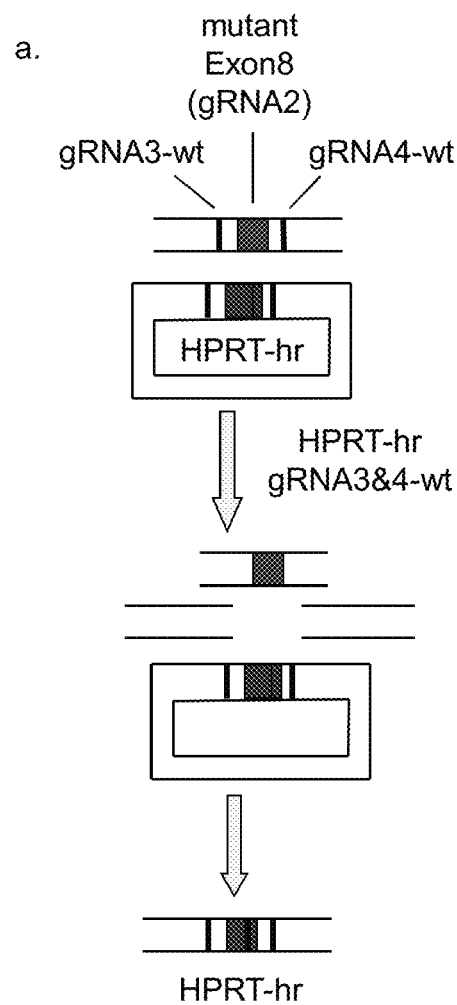
FIG. 1 (panels a through e) show the correction of the mutant HPRT gene by CRISPR-induced gene editing.
Figure 1:
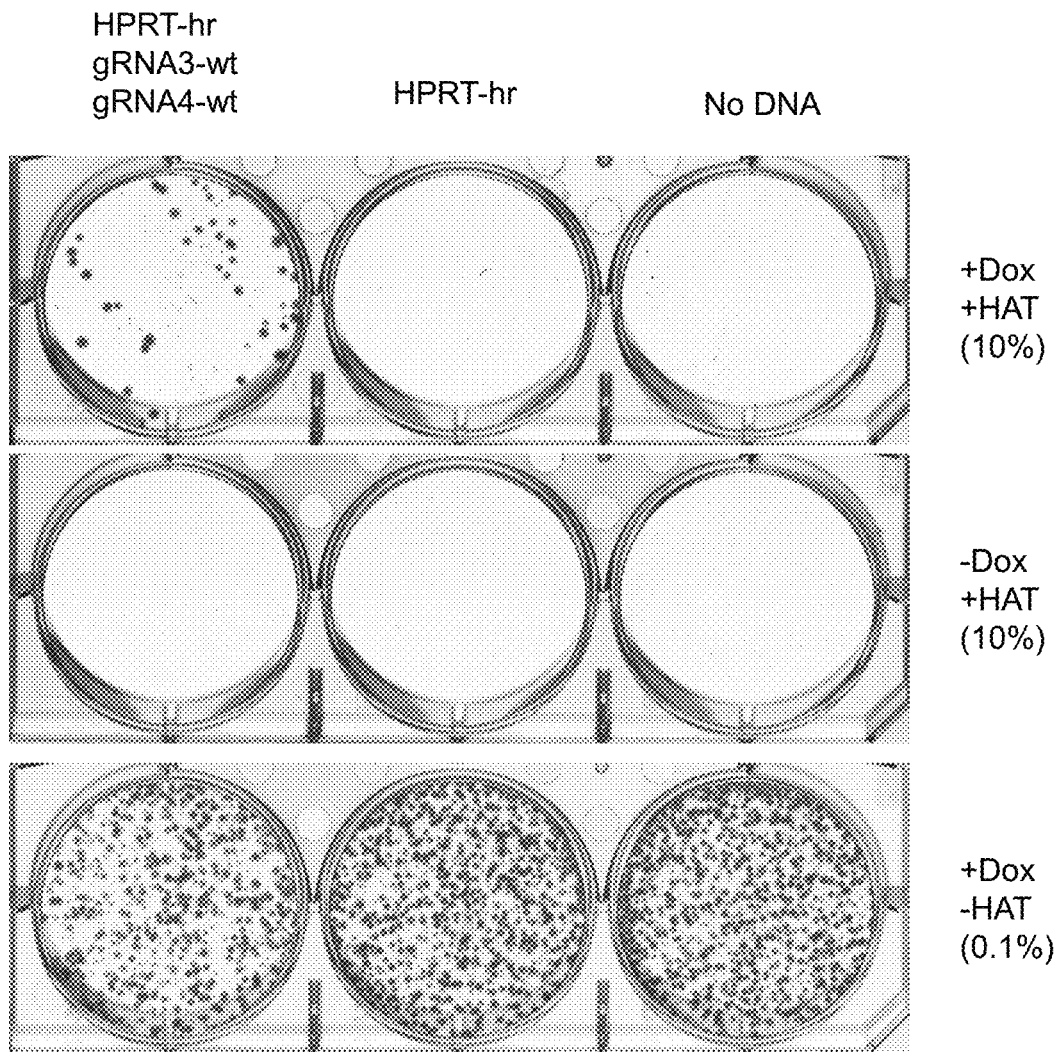
Figure 1:
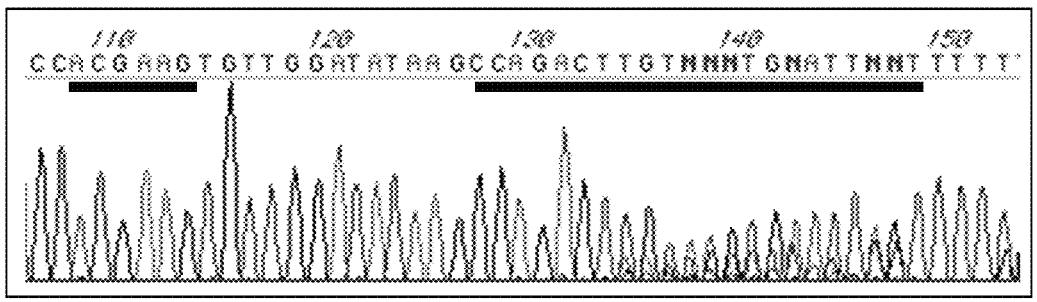
Figure 1:
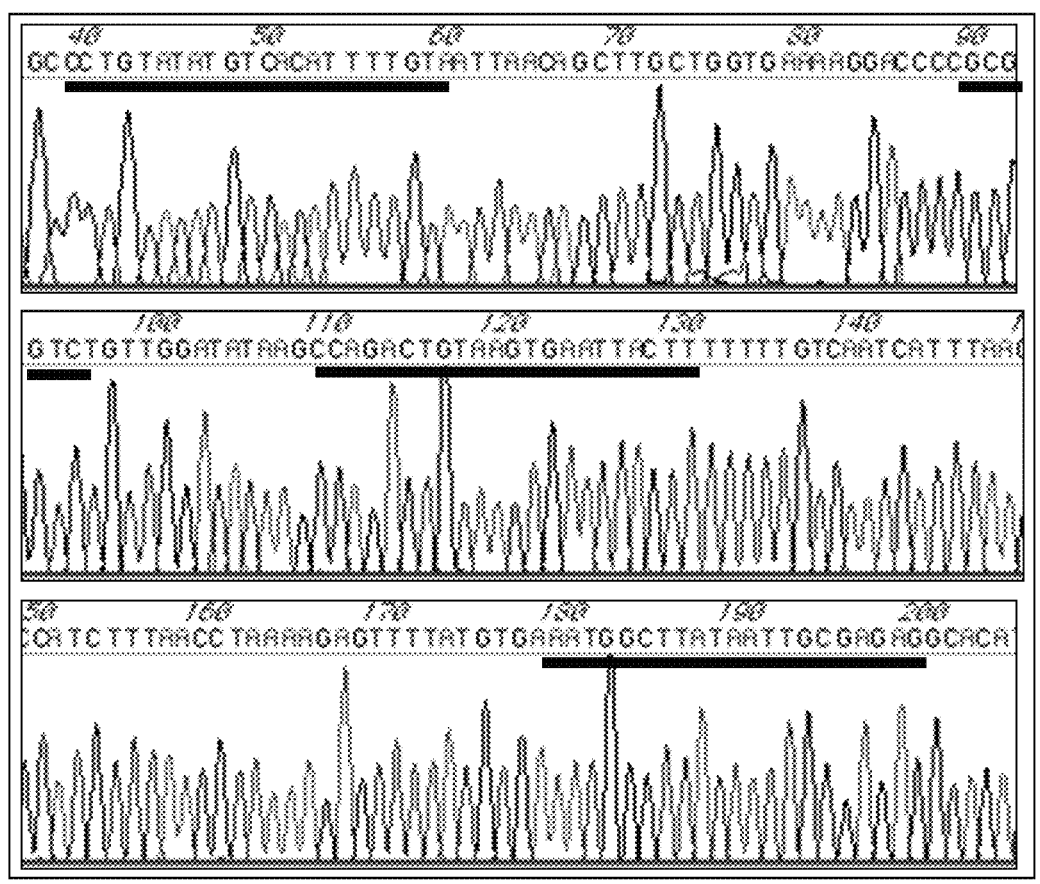

Various terms relating to embodiments of the present disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

It was hypothesized that HPRT mutations generated by gene co-targeting can be corrected by CRISPR-induced gene editing via homologous recombinational repair. If a gRNA against another gene of interest is co-expressed during HPRT gene editing, the corrected cells are enriched for mutations in the second gene. In accordance with the present disclosure, this hypothesis was tested and confirmed in human HCT116 cells. Furthermore, it was observed that with the proper gRNAs and homologous donors, the selection and counter-selection could be repeated indefinitely. Thus, HPRT co-targeting can be used to sequentially disrupt or edit as many genes as cell viability permits.

Compared to other enrichment methods, the various HPRT co-targeting methods in the present disclosure have several advantages including, for example: 1) They are highly efficient. For non-essential genes, it was observed that 80-100% of the 6-TG or HAT resistant cells have the gene of interest disrupted. 2) They only use basic tissue culture setup and standard transfection reagents. No sophisticated equipment, expensive reagents, or complicated protocols are required. 3) They are easy to scale up simply by increasing the number of transfections. 4) They do not involve viruses. Viruses can be difficult to prepare with consistent quality and take extra time to characterize. Viruses also raise concerns about biosafety in the laboratory and oncogenic effects of viral DNA integration into chromosomes if applied in the clinic. 5) They provide internal controls that allow a determination if a gene is essential or if two genes are synthetically lethal. 6) They provide internal controls that allow one to determine if a guide RNA is effective. 7) They leave no genetic imprint other than in the HPRT gene and the gene of interest. Guide RNAs (and Cas9) can be transiently expressed from plasmid DNA. The probability of plasmid DNA integration is low and can be easily excluded by checking for drug resistance conferred by the plasmids. 8) They allow disruption in an iterative and essentially "scar-free" way as many genes as cell viability permits. 9) They allow enrichment of cells that have been successfully edited to a pre-designed sequence.

The present disclosure provides methods for altering or editing one or more genes in a cell, and enriching cultures of the cell that comprise the altered or edited genes. The methods utilize CRISPR, along with CRISPR associated protein 9 (Cas9), which is an RNA-guided DNA endonuclease enzyme. The methods take advantage of the capacity to alter and restore the HPRT gene via Cas9-facilitated gene editing, and the capacity to use Cas9 nuclease to co-target a gene of interest along with HPRT. In some embodiments, the methods are carried out in vitro or ex vivo.

In some embodiments, the methods are carried out using Cas9-competent cells. This means that the cell expresses a functional Cas9 enzyme. The gene encoding the Cas9 enzyme may be integrated, including stably integrated, into the genome of the cell. In some embodiments, the gene encoding the Cas9 enzyme is provided to the cell, for example, by transfecting the cell with a gene encoding Cas9. The cell may be transfected, for example, with a plasmid encoding the Cas9 gene. The plasmid may further comprise a gRNA, for example, a gRNA that is to be used during targeting of HPRT or a gRNA that is to be used during targeting of a gene of interest. Thus, a gRNA-encoding plasmid may also comprise a gene encoding Cas9. The Cas9 gene in the plasmid may be operably linked to a constitutive promoter or operably linked to an inducible promoter, with the latter providing for control over Cas9 expression.

The methods may comprise first providing a Cas9-competent cell that comprises an altered HPRT. Alternately, the methods may comprise preparing a Cas9-competent cell by transfecting a cell with a gene encoding the Cas9 enzyme, e.g., on a plasmid.

Once a Cas9-competent cell is prepared or provided, the methods comprise altering or editing a target gene. In some embodiments, altering the target gene comprises utilizing a gRNA to direct the Cas9 nuclease to introduce a DSB in the target gene. The cell's natural, but error-prone DNA repair system will repair the ds break, but introduces an insertion or deletion or other alteration at the repair site, resulting in an altered target gene. In this case, the type of alteration is not controlled.

In order to control the alteration, the target gene may be edited. Thus, in some embodiments, the target gene is edited. Editing the target gene comprises utilizing a gRNA that hybridizes to a sequence of the target gene upstream of the intended site for editing, a gRNA that hybridizes to a sequence of the target gene downstream of the intended site for editing, and a nucleic acid comprising a donor sequence, with the donor sequence comprising one or more alterations of target gene that revise (edit) the target gene sequence in a controlled manner. In this way, the donor sequence may introduce one or more particular mutations in the target gene, including mutations that revise or correct one or more defects in the target gene.

The alteration or editing of the target gene is carried out in conjunction with parallel and concomitant Cas9-mediated altering and editing of the hypoxanthine guanine phosphoribosyl transferase (HPRT) gene. In this way, the state of the HPRT gene (e.g., altered, restored) can be used to select and counter-select cells. Cells comprising an altered HPRT gene (e.g., an alteration that causes the HPRT protein to not be expressed or that renders the HPRT protein non-functional) can be selected with 6-TG. Cells comprising a restored or wild type HPRT gene (e.g., HPRT protein is expressed and functional) can be selected with HAT. With the co-targeting of the target gene HPRT, the HPRT-selected cells comprise an altered or edited form of the HPRT gene, as well as an altered or edited form of the target gene. The cycle of altering and editing the HPRT gene along with a target gene of interest can be repeated as long as the cells will tolerate the target gene alterations.

In some embodiments, the methods comprise providing a Cas9-competent cell comprising an HPRT gene comprising an alteration. In some embodiments, the character of the alteration is such that the HPRT gene encodes a non-functional HPRT protein. The cell may then be co-transfected with a gRNA that hybridizes to a nucleic acid sequence of a target gene, thereby introducing an alteration to the target gene, a gRNA that hybridizes to the HPRT gene upstream of the HPRT gene alteration, a second gRNA that hybridizes to the HPRT gene downstream of the HPRT gene alteration, and a donor HPRT nucleic acid sequence that corrects the alteration and that lacks a sequence complementary to the sequence of either gRNA that hybridizes to the HPRT gene (e.g., lacks a sequence complementary to the aforementioned upstream and the downstream HPRT gRNA), and then culturing the cell in a medium comprising HAT. The gRNA and the donor nucleic acid sequence may be provided on a plasmid.

Following HAT selection, the cell may then be co-transfected with a gRNA that hybridizes to a nucleic acid sequence of a subsequent target gene, thereby introducing an alteration to the subsequent target gene, a gRNA that hybridizes to the HPRT gene, thereby re-introducing the alteration to the HPRT gene, and then cultured in a medium comprising 6-TG. The re-introduced alteration is preferably the same alteration from the Cas9 competent cell initially provided, though in some embodiments, the alteration is different from the alteration in the Cas9 competent cell initially provided.

Following 6-TG selection, the cell may then be co-transfected cell with a gRNA that hybridizes to a nucleic acid sequence of a subsequent target gene, thereby introducing an alteration to the subsequent target gene, a gRNA that hybridizes to the HPRT gene upstream of the HPRT gene alteration, a gRNA that hybridizes to the HPRT gene downstream of the HPRT gene alteration, and a donor nucleic acid comprising a wild type HPRT nucleic acid sequence that corrects the alteration, thereby restoring the HPRT gene to its wild type form, and then cultured in a medium comprising HAT. Alternately, the cell may be co-transfected with a gRNA that hybridizes to the HPRT gene upstream of the HPRT gene alteration, a gRNA that hybridizes to the HPRT gene downstream of the HPRT gene alteration, and a donor nucleic acid comprising a wild type HPRT nucleic acid sequence that corrects the alteration, thereby restoring the HPRT gene to its wild type form, and then cultured in a medium comprising HAT. In the former case, the cell will comprise multiple altered target genes, which, in some embodiments, are not the same gene, though it is possible to alter the same target gene in different locations (e.g., the target gene and the subsequent target gene are the same gene, which is edited at different locations). In the alternative case, the cell will comprise one fewer altered target gene. The gRNA and the donor nucleic acids may be provided on a plasmid.

In some embodiments, the target gene is edited instead of altered. In such embodiments, the methods comprise providing a Cas9-competent cell comprising an HPRT gene comprising an alteration. In some embodiments, the character of the alteration is such that the HPRT gene encodes a non-functional HPRT protein. The cell may then be co-transfected with a gRNA that hybridizes to a target gene upstream of a nucleic acid sequence of the target gene that is to be edited, a gRNA that hybridizes to the target gene downstream of the nucleic acid sequence of the target gene that is to be edited, a donor plasmid comprising a nucleic acid sequence that alters/edits the nucleic acid sequence of the target gene, a gRNA that hybridizes to the HPRT gene upstream of the HPRT gene alteration, a second gRNA that hybridizes to the HPRT gene downstream of the HPRT gene alteration, and a donor plasmid comprising a HPRT nucleic acid sequence that corrects the alteration and that lacks a sequence complementary to the sequence of each gRNA that hybridizes to the HPRT gene (e.g., lacks a sequence complementary to the aforementioned upstream and the downstream HPRT gRNA), then cultured in a medium comprising HAT. The gRNA and the donor nucleic acids may be provided on a plasmid.

Following HAT selection, the cell may then be transfected with a gRNA that hybridizes to the HPRT gene, thereby re-introducing the alteration to the HPRT gene, and then cultured in a medium comprising 6-TG. The re-introduced alteration is preferably the same alteration from the Cas9 competent cell initially provided, though in some embodiments, the alteration is different from the alteration in the Cas9 competent cell initially provided.

Following 6-TG selection, the cell may be co-transfected cell with a gRNA that hybridizes to a subsequent target gene upstream of a nucleic acid sequence of the subsequent target gene that is to be edited, a gRNA that hybridizes to the subsequent target gene downstream of the nucleic acid sequence of the subsequent target gene that is to be edited, a donor plasmid comprising a nucleic acid sequence that alters/edits the nucleic acid sequence of the subsequent target gene, a gRNA that hybridizes to the HPRT gene upstream of the HPRT gene alteration, a gRNA that hybridizes to the HPRT gene downstream of the HPRT gene alteration, and a donor nucleic acid comprising a wild type HPRT nucleic acid sequence that corrects the alteration, thereby restoring the HPRT gene to its wild type form, and then cultured in a medium comprising HAT. Alternately, the cell may be transfected with a gRNA that hybridizes to the HPRT gene upstream of the HPRT gene alteration, a gRNA that hybridizes to the HPRT gene downstream of the HPRT gene alteration, and a donor nucleic acid comprising a wild type HPRT nucleic acid sequence that corrects the silent alteration, thereby restoring the HPRT gene to its wild type form, and then cultured in a medium comprising HAT. In the former case, the cell will comprise multiple edited target genes, which, in some embodiments, are not the same gene, though it is possible to edit the same target gene in different locations (e.g., the target gene and the subsequent target gene are the same gene, which is edited at different locations). In the alternative case, the cell will comprise one fewer altered target gene. The gRNA and the donor nucleic acids may be provided on a plasmid.

The method steps may be repeated any number of times, in order to alter or edit as many target genes or locations within a target gene or target genes as is desired or as the cell will tolerate. The number of repeats may be constrained, for example, by the type of genes being altered. The target gene (e.g., the first target gene and each subsequent target gene) is not critical, and can vary according to the needs or desires of the investigator. Repeating of the method may conclude when no further altering or editing of the target gene(s) is desired or possible. The method thus may be concluded by restoring HPRT to its wild type form, such as in the alternate steps described above, whereby the HPRT gene is edited to wild type form but without the concomitant editing or alteration of a target gene.

In some embodiments, the methods comprise co-transfecting a Cas9-competent cell with a gRNA that hybridizes to a nucleic acid sequence of a target gene, thereby introducing an alteration in the target gene, and a gRNA that hybridizes to a nucleic acid sequence of the HPRT gene, thereby introducing an alteration to the HPRT gene, and then culturing the cell in a medium comprising 6-TG.

Following 6-TG selection, the cell may be co-transfected cell with a gRNA that hybridizes to a nucleic acid sequence of a subsequent target gene, thereby introducing an alteration in the subsequent target gene, and a gRNA that hybridizes to the HPRT gene upstream of the HPRT gene alteration, a gRNA that hybridizes to the HPRT gene downstream of the HPRT gene alteration, and a donor nucleic acid comprising a HPRT nucleic acid sequence that corrects the alteration and that lacks a sequence complementary to the sequence of gRNA that hybridize upstream and downstream of the alteration, and then cultured in a medium comprising HAT.

Following HAT selection, the cell may be co-transfected with the gRNA that hybridizes to the HPRT gene, thereby re-introducing the alteration in the HPRT gene, and a gRNA that hybridizes to a nucleic acid sequence of a subsequent target gene, thereby introducing an alteration in the subsequent target gene, and then cultured in a medium comprising 6-TG.

Following the 6-TG selection, the cell may be co-transfected with a gRNA that hybridizes to a nucleic acid sequence of a subsequent target gene, thereby introducing an alteration in the subsequent target gene, and the gRNA that hybridizes to the HPRT gene upstream of the HPRT gene alteration, the gRNA that hybridizes to the HPRT gene downstream of the HPRT gene alteration, and the donor nucleic acid comprising a HPRT nucleic acid sequence comprising a wild type HPRT nucleic acid sequence that corrects the alteration, thereby restoring the HPRT gene to its wild type form, and then cultured in a medium comprising HAT.

The cells may comprise a cell line. The cells may also comprise primary isolates. The primary isolates may be obtained from any animal, including farm animals, companion animals, lab animals, and non-human primates. In some embodiments, the primary isolates are from human beings. The primary isolates may be obtained from any tissue, organ, or system in the body. In some embodiments, the cells, having been edited according to the methods described or exemplified herein, may be placed back into the body of the animal from which they were obtained, in edited form.

In accordance with the methods, the gRNA that hybridizes to the HPRT gene that introduces an alteration in the HPRT gene may comprise the nucleic acid sequence of SEQ ID NO:25. The gRNA that hybridizes to the HPRT gene upstream of the alteration may comprise the nucleic acid sequence of SEQ ID NO:1 or SEQ ID NO:3, and the gRNA that hybridizes to the HPRT gene downstream of the HPRT gene alteration may comprise the nucleic acid sequence of SEQ ID NO:2 or SEQ ID NO:4.

In some embodiments, the donor plasmid comprising a wild type-restoring HPRT nucleic acid sequence may comprise the nucleic acid sequence of SEQ ID NO:22. In some embodiments, the donor plasmid comprising an altered nucleic acid sequence of the HPRT gene comprises the nucleic acid sequence of SEQ ID NO:21. In some embodiments, a plasmid comprising a gRNA for disrupting the HPRT gene comprises the nucleic acid sequence of SEQ ID NO:20.

Plasmids for transfection of a cell to comprise an altered HPRT sequence are provided. The plasmids may comprise the nucleic acid sequence of SEQ ID NO:21. The plasmids may comprise the nucleic acid sequence of SEQ ID NO:20.

Plasmids for transfection of a cell to comprise a wild type HPRT sequence or restored wild type HPRT sequence are provided. The plasmids may comprise the nucleic acid sequence of SEQ ID NO:24 or SEQ ID NO:25. The plasmids may comprise the nucleic acid sequence of SEQ ID NO:21 or SEQ ID NO:22.

Cells transfected with a plasmid comprising the nucleic acid sequence of SEQ ID NO:20, SEQ ID NO:21, SEQ ID NO:22, SEQ ID NO:23, or SEQ ID NO:24 are provided. The cells may be further transfected with a plasmid encoding a gRNA. The cells may be further transfected with a plasmid encoding Cas9. The cells may be Cas9 competent cells.

Kits comprising one or more plasmids are provided. In some embodiments, a kit comprises three plasmids, one comprising the nucleic acid sequence of SEQ ID NO:20, one comprising the nucleic acid sequence of SEQ ID NO:21, and one comprising the nucleic acid sequence of SEQ ID NO:22. The kits may further comprise instructions for using the plasmid(s) in a method for editing one or more genes in a cell, and/or enriching cultures of the cell that comprise the edited genes. The kits may further comprise HAT or a media comprising HAT. The kits may further comprise 6GT or a media comprising 6GT.

The following representative embodiments are presented:

Embodiment 1

A plasmid, comprising the nucleic acid sequence of SEQ ID NO: 20.

Embodiment 2

A plasmid, comprising the nucleic acid sequence of SEQ ID NO: 21.

Embodiment 3

A plasmid, comprising the nucleic acid sequence of SEQ ID NO: 22.

Embodiment 4

A cell transfected with the plasmid of any one of embodiments 1 to 3.

Embodiment 5

A kit, comprising two or more of a plasmid having the nucleic acid sequence of SEQ ID NO: 20, a plasmid having the nucleic acid sequence of SEQ ID NO: 21, and a plasmid having the nucleic acid sequence of SEQ ID NO: 22, and optionally further comprising a gRNA comprising the nucleic acid sequence of SEQ ID NO: 25, SEQ ID NO: 1, SEQ ID NO: 2, SEQ ID NO: 3, or SEQ ID NO: 4.

Embodiment 6

A nucleic acid, comprising the nucleic acid sequence of SEQ ID NO: 23 or the complement thereof.

Embodiment 7

A nucleic acid, comprising the nucleic acid sequence of SEQ ID NO: 24 or the complement thereof.

Embodiment 8

A nucleic acid, comprising the nucleic acid sequence of SEQ ID NO: 25, SEQ ID NO: 1, SEQ ID NO: 2, SEQ ID NO: 3, or SEQ ID NO: 4, or the complement thereof.

Embodiment 9

A method, comprising: (a) providing a Cas9-competent cell comprising a hypoxanthine guanine phosphoribosyl transferase (HPRT) gene comprising an alteration; (b) co-transfecting the cell with a guide RNA (gRNA) that hybridizes to a nucleic acid sequence of a target gene, a first gRNA that hybridizes to the HPRT gene upstream of the alteration, a second gRNA that hybridizes to the HPRT gene downstream of the alteration, and a first donor plasmid comprising a HPRT nucleic acid sequence that corrects the alteration and that lacks a sequence complementary to the sequence of first and second gRNA that hybridizes to the HPRT gene, and then culturing the cell in a medium comprising hypoxanthine-aminopterin-thymidine (HAT); (c) transfecting the cell with a third gRNA that hybridizes to the HPRT gene, thereby re-introducing the alteration to the HPRT gene, and then culturing the cell in a medium comprising 6-thioguanine; and (d) co-transfecting the cell with a gRNA that hybridizes to a nucleic acid sequence of a subsequent target gene, a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild-type form, and then culturing the cell in a medium comprising HAT; or (e) co-transfecting the cell with a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild-type form, and then culturing the cell in a medium comprising HAT.

Embodiment 10

The method according to embodiment 9, further comprising repeating step (c), and thereafter repeating steps (b) through (d) a plurality of times, wherein the target gene in step (b) is a different gene each time step (b) is repeated and wherein the subsequent target gene in step (d) is both different from the target gene in step (b) and is a different gene each time step (d) is repeated.

Embodiment 11

The method according to embodiment 9 or 10, wherein the Cas9-competent cell comprises Cas9 integrated into its genome.

Embodiment 12

The method according to embodiment 9 or 10, wherein the Cas9-competent cell has been transfected with a plasmid encoding Cas9.

Embodiment 13

The method according to any one of embodiments 9 to 12, wherein the first donor plasmid comprises the nucleic acid sequence of SEQ ID NO: 21.

Embodiment 14

The method according to any one of embodiments 9 to 13, wherein the second donor plasmid comprises the nucleic acid sequence of SEQ ID NO: 22.

Embodiment 15

The method according to any one of embodiments 9 to 14, wherein the HPRT nucleic acid sequence that corrects the alteration and that lacks a sequence complementary to the sequence of first and second gRNA that hybridizes to the HPRT gene comprises the nucleic acid sequence of SEQ ID NO: 23.

Embodiment 16

The method according to any one of embodiments 9 to 15, wherein the wild type HPRT nucleic acid sequence comprises the nucleic acid sequence of SEQ ID NO: 24.

Embodiment 17

The method according to any one of embodiments 9, 10, or 12 to 16, wherein the Cas9-competent cell is a cell isolated from a non-human mammal.

Embodiment 18

The method according to any one of embodiments 9, 10, or 12 to 16, wherein the Cas9-competent cell is a cell isolated from a human being.

Embodiment 19

The method according to embodiment 12, wherein the plasmid encoding Cas9 comprises an inducible promoter operably linked to Cas9.

Embodiment 20

A method, comprising: (a) co-transfecting a Cas9-competent cell with a guide RNA (gRNA) that hybridizes to a nucleic acid sequence of a target gene and a first gRNA that hybridizes to a nucleic acid sequence of the HPRT gene, thereby introducing an alteration to the HPRT gene, and then culturing the cell in a medium comprising 6-thioguanine; (b) co-transfecting the cell with a second gRNA that hybridizes to the HPRT gene upstream of the alteration, a third gRNA that hybridizes to the HPRT gene downstream of the alteration, and a first donor plasmid comprising a HPRT nucleic acid sequence that corrects the alteration but lacks a sequence complementary to the sequence of second and third gRNA, and optionally, a guide RNA (gRNA) that hybridizes to a nucleic acid sequence of a subsequent target gene, and then culturing the cell in a medium comprising HAT; (c) co-transfecting the cell with the first gRNA, thereby re-introducing the alteration to the HPRT gene, and a gRNA that hybridizes to a nucleic acid sequence of a subsequent target gene, and then culturing the cell in a medium comprising 6-thioguanine; and (d) co-transfecting the cell with a fourth gRNA that hybridizes to the HPRT gene upstream of the alteration, a fifth gRNA that hybridizes to the HPRT gene downstream of the alteration, and a second donor plasmid comprising a HPRT nucleic acid sequence comprising a wild type HPRT nucleic acid sequence that corrects the alteration, and optionally a guide RNA (gRNA) that hybridizes to a nucleic acid sequence of a subsequent target gene, and then culturing the cell in a medium comprising HAT.

Embodiment 21

The method according to embodiment 20, further comprising (e) repeating step (c) and thereafter repeating steps (b) through (d) and, optionally, repeating step (e) a plurality of additional times.

Embodiment 22

The method according to embodiment 21, wherein the subsequent target gene in step (c) is a different gene each time step (c) is repeated and wherein each subsequent target gene in step (c) is different from the target gene in step (a).

Embodiment 23

The method according to any one of embodiment 20-22, wherein the Cas9-competent cell comprises Cas9 integrated into its genome.

Embodiment 24

The method according to any one of embodiments 20-22, wherein the Cas9-competent cell has been transfected with a plasmid encoding Cas9.

Embodiment 25

The method according to any one of embodiments 20-24, wherein the first donor plasmid comprises the nucleic acid sequence of SEQ ID NO: 21.

Embodiment 26

The method according to any one of embodiments 20-25, wherein the second donor plasmid comprises the nucleic acid sequence of SEQ ID NO: 22.

Embodiment 27

The method according to any one of embodiments 20-26, wherein the HPRT nucleic acid sequence that corrects the alteration but lacks a sequence complementary to the sequence of second and third gRNA comprises the nucleic acid sequence of SEQ ID NO: 23.

Embodiment 28

The method according to any one of embodiments 20-27, wherein the wild type HPRT nucleic acid sequence comprises the nucleic acid sequence of SEQ ID NO: 24.

Embodiment 29

The method according to any one of embodiments 20-22, or 24 to 28, wherein the Cas9-competent cell is a cell isolated from a non-human mammal.

Embodiment 30

The method according to any one of embodiments 20-22, or 24 to 28, wherein the Cas9-competent cell is a cell isolated from a human being.

Embodiment 31

The method according to embodiment 24, wherein the plasmid encoding Cas9 comprises an inducible promoter operably linked to Cas9.

Embodiment 32

A method, comprising: (a) providing a Cas9-competent cell comprising a hypoxanthine guanine phosphoribosyl transferase (HPRT) gene comprising an alteration; (b) co-transfecting the cell with a first guide RNA (gRNA) that hybridizes upstream of a nucleic acid sequence of a target gene, a second gRNA that hybridizes downstream of the nucleic acid sequence of the target gene, a first donor plasmid comprising a nucleic acid sequence that alters the nucleic acid sequence of the target gene, a first gRNA that hybridizes to the HPRT gene upstream of the alteration, a second gRNA that hybridizes to the HPRT gene downstream of the alteration, and a first donor plasmid comprising a HPRT nucleic acid sequence that corrects the alteration and that lacks a sequence complementary to the sequence of first and second gRNA that hybridizes to the HPRT gene, and then culturing the cell in a medium comprising hypoxanthine-aminopterin-thymidine (HAT); (c) transfecting the cell with a third gRNA that hybridizes to the HPRT gene, thereby re-introducing the alteration to the HPRT gene, and then culturing the cell in a medium comprising 6-thioguanine; and (d) co-transfecting the cell with a first gRNA that hybridizes upstream of a nucleic acid sequence of a subsequent target gene, a second gRNA that hybridizes downstream of the nucleic acid sequence of the subsequent target gene, and a first donor plasmid comprising a nucleic acid sequence that alters the nucleic acid sequence of the subsequent target gene, a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild-type form, and then culturing the cell in a medium comprising HAT; or (e) co-transfecting the cell with a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild-type form, and then culturing the cell in a medium comprising HAT.

Embodiment 33

The method according to embodiment 32, further comprising repeating step (c), and thereafter repeating steps (b) through (d) a plurality of times, wherein the target gene in step (b) is a different gene each time step (b) is repeated and wherein the subsequent target gene in step (d) is both different from the target gene in step (b) and is a different gene each time step (d) is repeated.

Embodiment 34

The method according to embodiment 32 or 33, wherein the Cas9-competent cell comprises Cas9 integrated into its genome.

Embodiment 35

The method according to embodiment 32 or 33, wherein the Cas9-competent cell has been transfected with a plasmid encoding Cas9.

Embodiment 36

The method according to any one of embodiments 32 to 35, wherein the first donor plasmid comprising a HPRT nucleic acid sequence that corrects the alteration comprises the nucleic acid sequence of SEQ ID NO: 21.

Embodiment 37

The method according to any one of embodiments 32 to 36, wherein the second donor plasmid comprising a HPRT nucleic acid sequence that corrects the alteration comprises the nucleic acid sequence of SEQ ID NO: 22.

Embodiment 38

The method according to any one of embodiments 32 to 37, wherein the HPRT nucleic acid sequence that corrects the alteration and that lacks a sequence complementary to the sequence of first and second gRNA that hybridizes to the HPRT gene comprises the nucleic acid sequence of SEQ ID NO: 23.

Embodiment 39

The method according to any one of embodiments 32 to 38, wherein the wild type HPRT nucleic acid sequence comprises the nucleic acid sequence of SEQ ID NO: 24.

Embodiment 40

The method according to any one of embodiments 32, 33, or 35 to 49, wherein the Cas9-competent cell is a cell isolated from a non-human mammal.

Embodiment 41

The method according to any one of embodiments 32, 33, or 35 to 49, wherein the Cas9-competent cell is a cell isolated from a human being.

Embodiment 42

The method according to embodiment 35, wherein the plasmid encoding Cas9 comprises an inducible promoter operably linked to Cas9.

Embodiment 43

A vector, comprising the nucleic acid sequence of SEQ ID NO: 23.

Embodiment 44

A vector, comprising the nucleic acid sequence of SEQ ID NO: 24.

Embodiment 45

A vector, comprising the nucleic acid sequence of SEQ ID NO: 25.

Embodiment 46

A cell transfected with the vector of any one of embodiments 43 to 45.

Embodiment 47

A kit, comprising two or more of the vector of any one of embodiments 43 to 45.

The following examples are provided to describe the embodiments in greater detail. They are intended to illustrate, not to limit, the present disclosure.

EXAMPLES

Example 1: General Experimental Methods

Cell culture and reagents. The human HCT116 cells, Dulbecco's Modified Eagle Medium (DMEM), penicillin/streptomycin (P/S), L-glutamine, non-essential amino acids (NEAA), and G418 were obtained from an in-house Tissue Culture Facility. Cas9-expressing HCT116 cells were constructed. Cells were grown in DMEM supplemented with 10% FBS, 2 mM L-glutamine, NEAA, and P/S at 37° C. under a 5% $CO_2$ humidified atmosphere.

Doxycycline and doxycycline-free fetal bovine serum were purchased from Clonetech (Takara-Clonetech, CA). HAT media, HT media, 6-thioguanine, Crystal violet were purchased from Sigma-Aldrich (MO).

Construction of Plasmids Expressing Guide RNAs.

The 19 nt gRNA sequences used in this study have been described in Liao et al., Nucleic Acids Res., 2015, 43, e134, except the following (5'-(N)19NGG-3' strand):

```
(HPRTg3)
                                         (SEQ ID NO: 1)
AACATACAGAGAGACTACA, (HPRTg4)
                                         (SEQ ID NO: 2)
TTAGAGAATATTTGTAGAG, (HPRTg3-hr)
                                         (SEQ ID NO: 3)
ACAAAATGTGACATATACA,
and (HPRTg4-hr)
                                         (SEQ ID NO: 4)
AATGGCTTATAATTGCGAG.
```

Primers for PCR amplification of genomic DNA are (5'->3'):

```
HPRT:
                                         (SEQ ID NO: 5)
TGGGCAACAGAGCGAGATTC,
and (SEQ ID NO: 6)
ATCAAAGTGGGAGGCCAGTG, Exo1:
                                         (SEQ ID NO: 7)
TCCAGTTCCAGCTGCCTAGA,
and (SEQ ID NO: 8)
GTCTGCACATTCCTAGCCGA, AAVS1:
                                         (SEQ ID NO: 9)
ACAGGAGGTGGGGGTTAGAC,
and (SEQ ID NO: 10)
TATATTCCCAGGGCCGGTTA,
and Trex1:
                                         (SEQ ID NO: 11)
GCAGACCCTCATCTTTTTCG.
```

The donor sequences are: HPRT-wt (chromosome X: 134,497,859-134,499,210) and HPRT-hr (chromosome X: 134,497,915-134,499,152 with the indicated modifications). The gRNA oligonucleotides were subcloned into a vector carrying the U6 promoter. The donor sequences were subcloned into a modified pUC19 vector.

Guide RNA Targeting in Cells.

Plasmids were introduced into HCT116-Cas9 cells (in 24-well, 95-99% confluency) by transfection with lipofectamine 2000 (Invitrogen, CA) following the manufacturer's protocol. 10% of the cells were re-seeded 14 hours post transfection with or without doxycycline (1 µg/ml). After 3-4 days of growth, they were reseeded in DMEM media in 6-well plates at various densities with or without HAT (1x) or 6-TG (1 µg/ml). For HAT selection, the media was changed to HT (1x) media after four days and then to regular DMEM after three more days. Cells were grown for a total of 10 days and then passaged or stained with Crystal Violet. The HAT-selected cells were subject to another round of HAT/HT treatment to remove the residual 6-TG resistant cells.

Amplification of the Targeted Regions.

Genomic DNA was extracted from cells as previously described in Liao et al., Nucleic Acids Res., 2015, 43, e134. The targeted regions were amplified from genomic DNA with Hot Start Taq DNA polymerase (NEB, MA) with the following primers (5'->3'):

```
HRPT:
                                    (SEQ ID NO: 12)
GATGCTCACCTCTCCCACAC,
and (SEQ ID NO: 13)
ACATCCATGGGACTTCTGCC;

AAVS1:
                                    (SEQ ID NO: 14)
ACAGGAGGTGGGGGTTAGAC,
and (SEQ ID NO: 15)
TATATTCCCAGGGCCGGTTA;

Trex1:
                                    (SEQ ID NO: 16)
GCAGACCCTCATCTTTTTCG,
and (SEQ ID NO: 17)
TACTGGGCTCAGATAGTTGAC, Exo1:
                                    (SEQ ID NO: 18)
TCCAGTTCCAGCTGCCTAGA,
and (SEQ ID NO: 19)
GTCTGCACATTCCTAGCCGA.
```

All oligonucleotides were synthesized by Integrated DNA technologies (IA).

Example 2: Results

HPRT mutations can be corrected by CRISPR-induced homologous recombination repair. It was first tested if the mutations in exon 8 of the HPRT gene in the co-targeted cells could be corrected by CRISPR-induced gene editing. Two gRNAs were designed to direct Cas9 to clip out the mutant exon 8 of the HPRT gene in the genome (see, FIG. 1, panel a). The homologous donor (HPRT-hr) is a modified 1 kb fragment of the HPRT genomic DNA that lacks the targets for the two editing gRNAs but contains the wild type open reading frame with a few silent mutations for tracking (see, FIG. 1, panel a).

Co-transfection of the plasmids for the two editing gRNAs and the HPRT-hr donor plasmid into HPRT⁻ HCT116 cells that express Cas9 from a doxycycline-inducible promoter generated many HAT resistant cells (see, FIG. 1, panel b). No cells survived if the guide RNA plasmids or doxycycline were omitted. The genomic DNA of the HAT resistant cells was then isolated and the region containing exon 8 was amplified with a pair of primers outside the donor sequence. As shown in FIG. 1 (panels c through e), the mutant HPRT region was indeed edited into a sequence identical to that of the donor. These observations demonstrated that the mutant HPRT gene could be corrected by CRISPR-induced gene editing.

Figure 2:
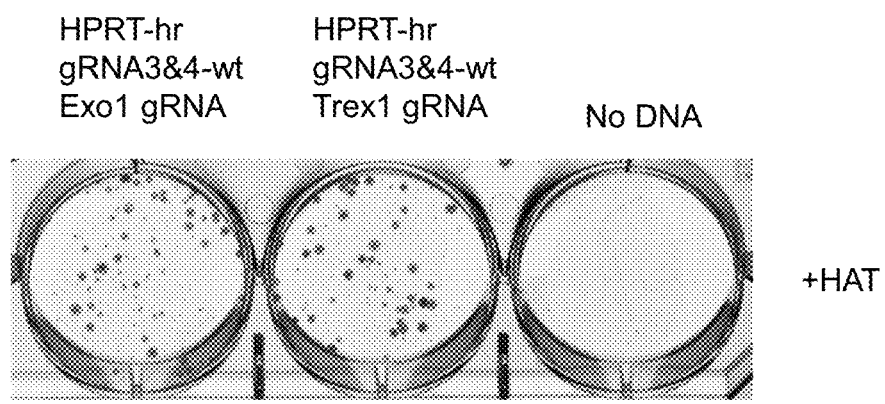
FIG. 2 (panels a and b) show co-targeting of Exo1 and Trex1 genes during HPRT gene editing.
Figure 2:
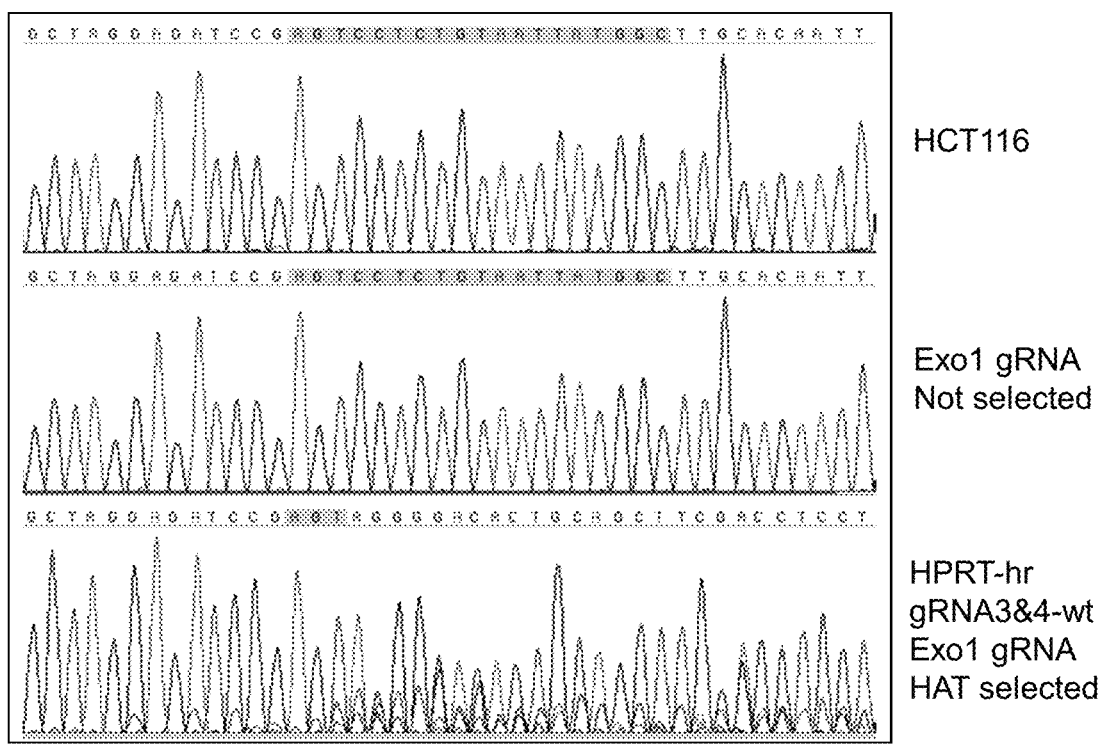
Figure 2:
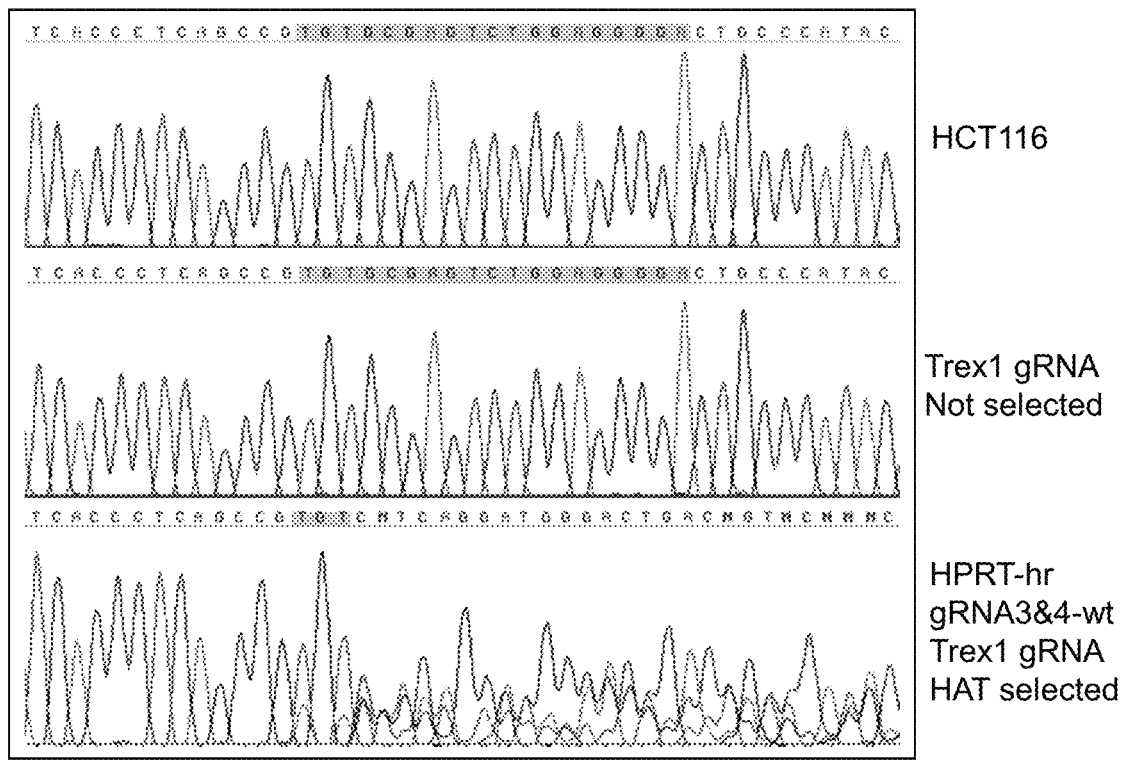

HPRT gene editing can be used for the co-targeting of another gene. The HAT resistant cells were competent for CRISPR, so it was tested if co-expressing a gRNA targeting another gene might lead to the enrichment of cells that had also disrupted this other gene. Cas9-expressing HPRT⁻ cells were co-transfected with the HPRT-hr donor plasmid and plasmids that express respectively the two editing gRNAs and a gRNA targeting the Exo1 gene or Trex1 gene. Genomic DNA was isolated from the HAT resistant cells and the Exo1 region was amplified by PCR. As shown in FIG. 2 (panels a through c), the Exo1 and Trex1 target regions were heavily mutated. In contrast, cells that were transfected with the Exo1 gRNA or Trex1 gRNA plasmids but not selected by HAT showed no detectable mutations. These data demonstrate that HPRT gene editing can be used as an effective enrichment method for the co-targeting of another gene.

Figure 3:
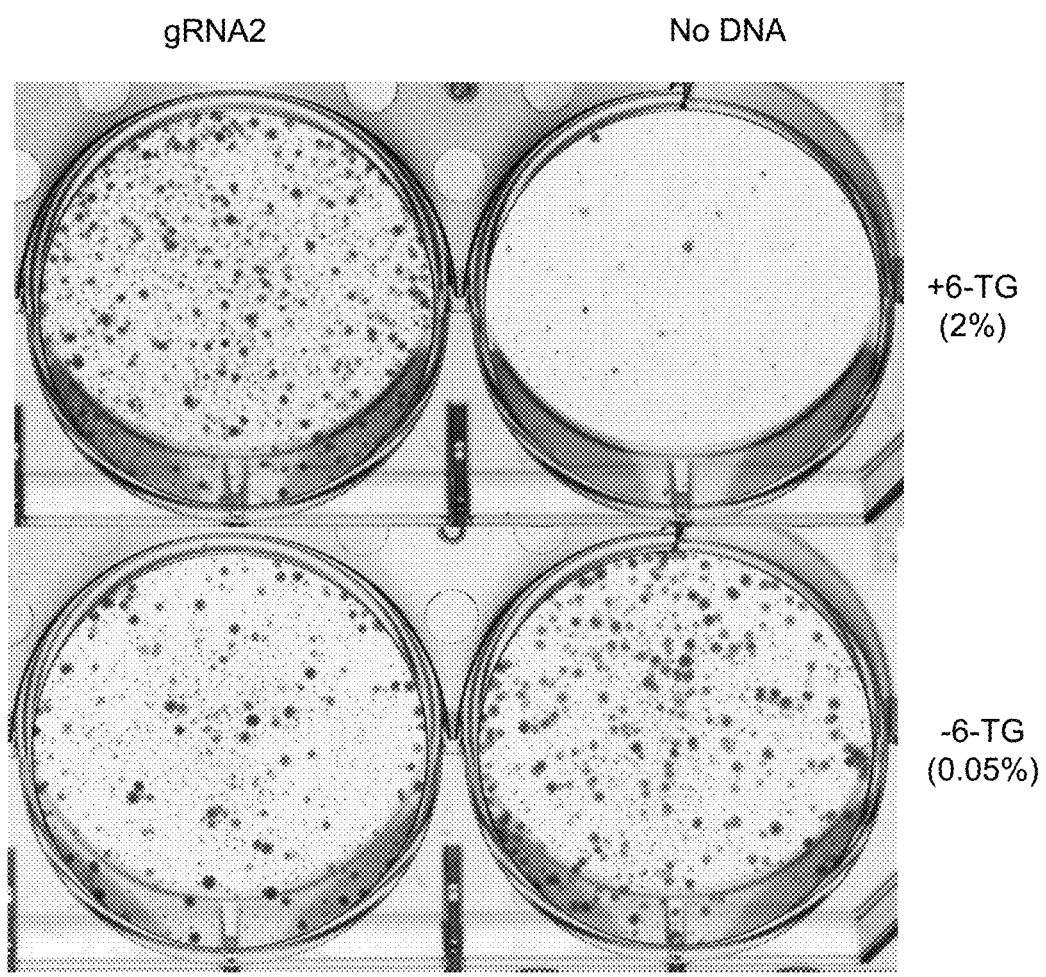
FIG. 3 (panels a, b, and c) show re-disruption and re-editing of the HPRT gene.
Figure 3:
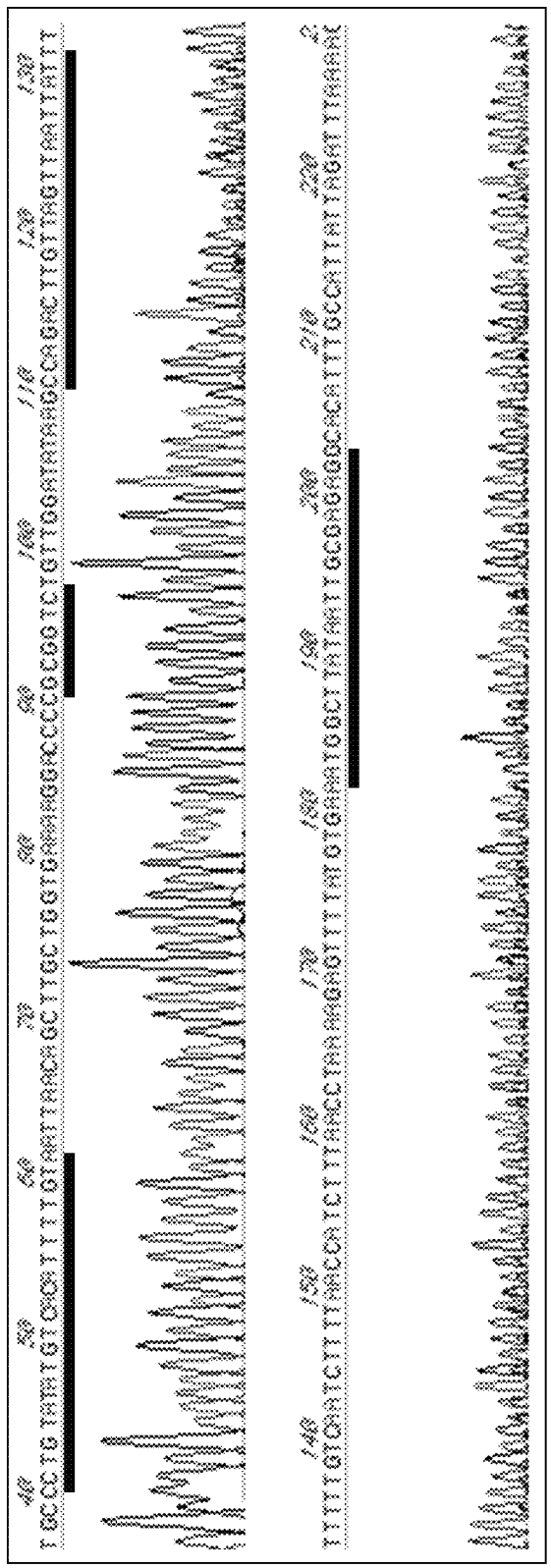
Figure 3:
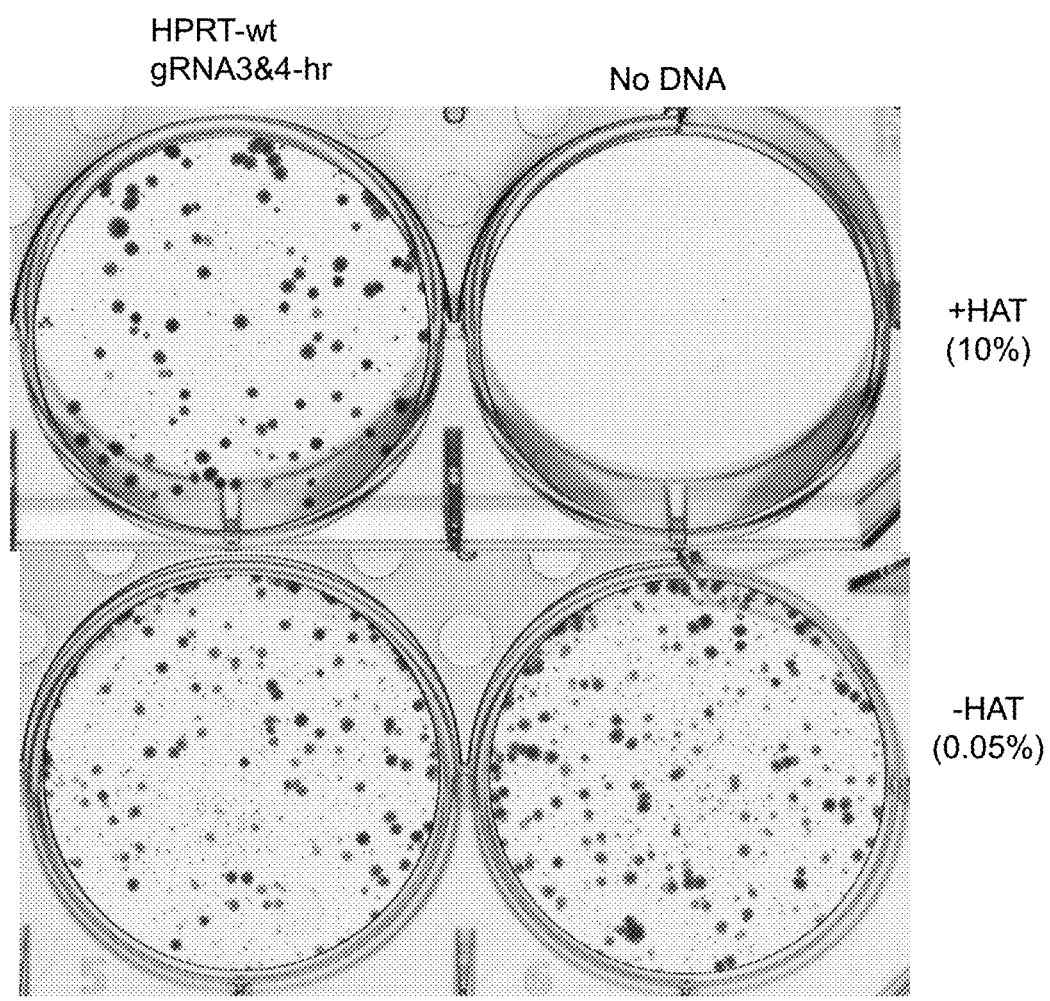
Figure 3:
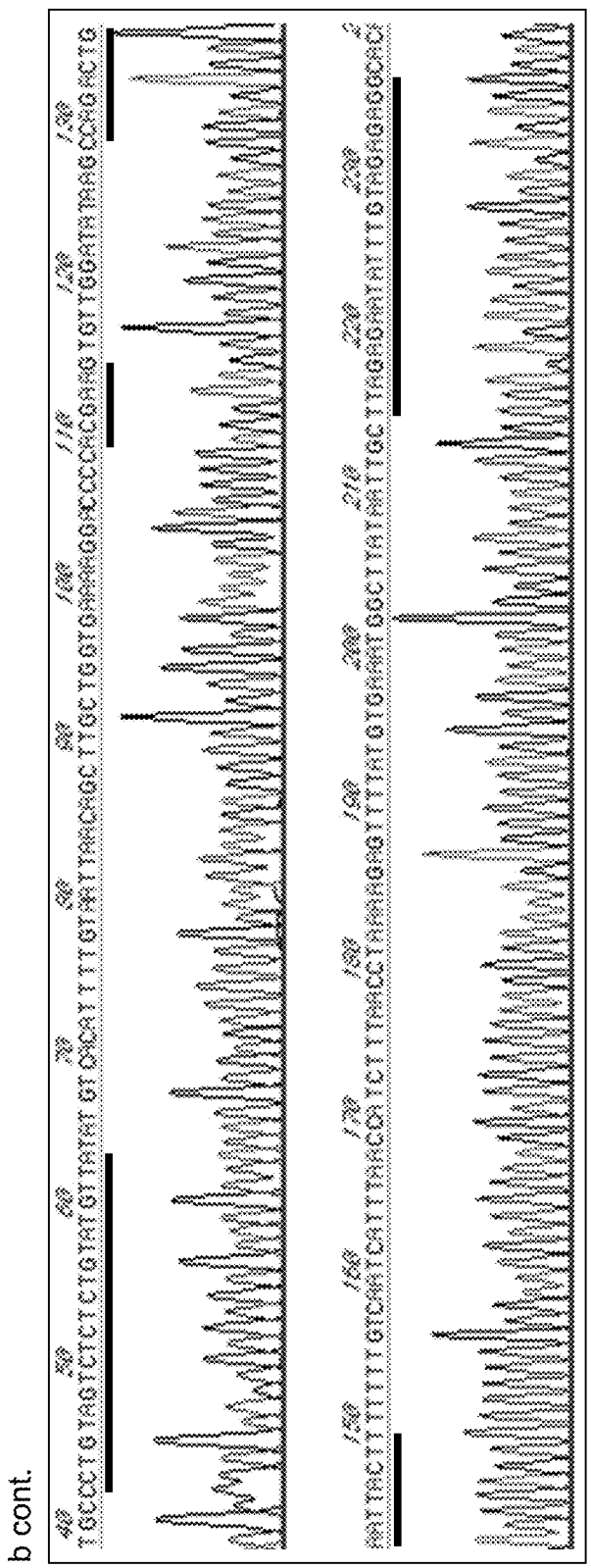

CRISPR-induced disruption and correction of the HPRT gene can be repeated indefinitely. The corrected cells had restored the target for the original gRNA used to disrupt the HPRT gene. Therefore they could be made into HPRT-mutant cells again with the same gRNA, giving rise to 6-TG resistant cells (see, FIG. 3, panel a). However, the targets for the two editing gRNAs were no longer intact, with only PAM and the adjacent 3 nucleotides before the Cas9 cleavage site still remaining. As such, the re-disrupted HPRT gene could no longer be corrected with the same two editing gRNAs.

Two new editing gRNAs were designed, with each incorporating the same PAM, the 3 nucleotides before the cleavage site, and the new 16 nucleotides after the cleavage site. The predicted positions of Cas9 cleavage were exactly the same as those of the original editing gRNAs. Accordingly, the original wild type HPRT sequence, which lacks the targets for the new editing gRNAs, was used as the new donor (HPRT-wt). With the new editing gRNAs and donor, HAT resistant cells were readily obtained from the re-disrupted HPRT gene (see, FIG. 3, panel b). Analysis of the genomic DNA isolated from these cells showed that the HPRT target region was corrected to the original wild type sequence (see, FIG. 3, panel c). Therefore, the four-step cycle of HPRT disruption and correction can be repeatedly indefinitely.

Figure 4:
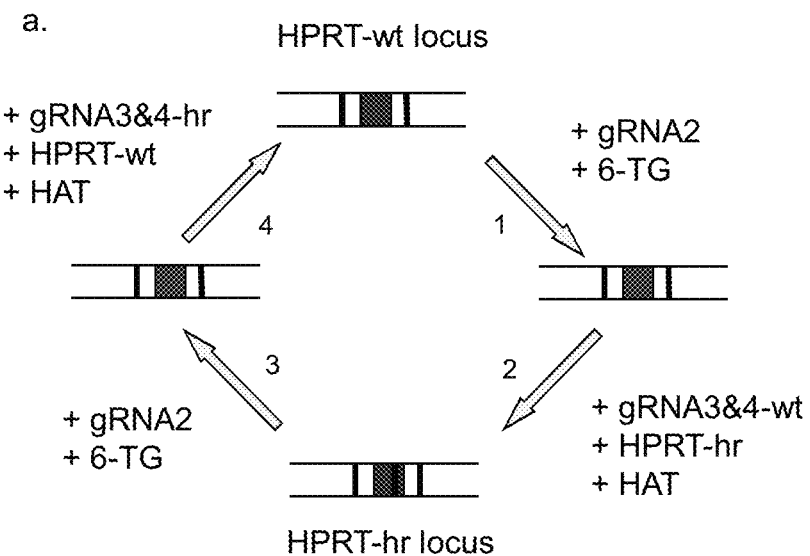
FIG. 4 (panels a, b, and c) show iterative disruption of multiple genes by co-targeting the HPRT gene in a cyclic way.
Figure 4:
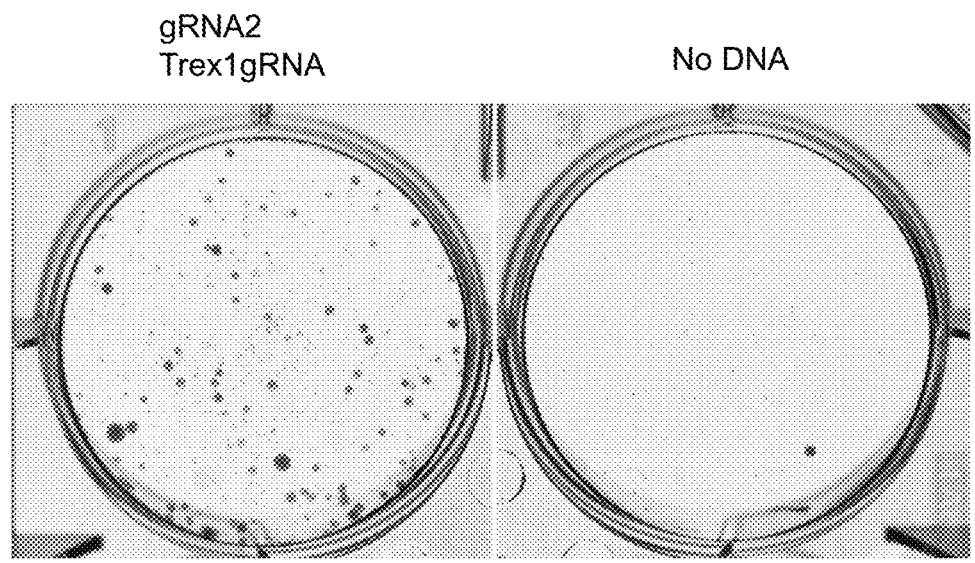
Figure 4:
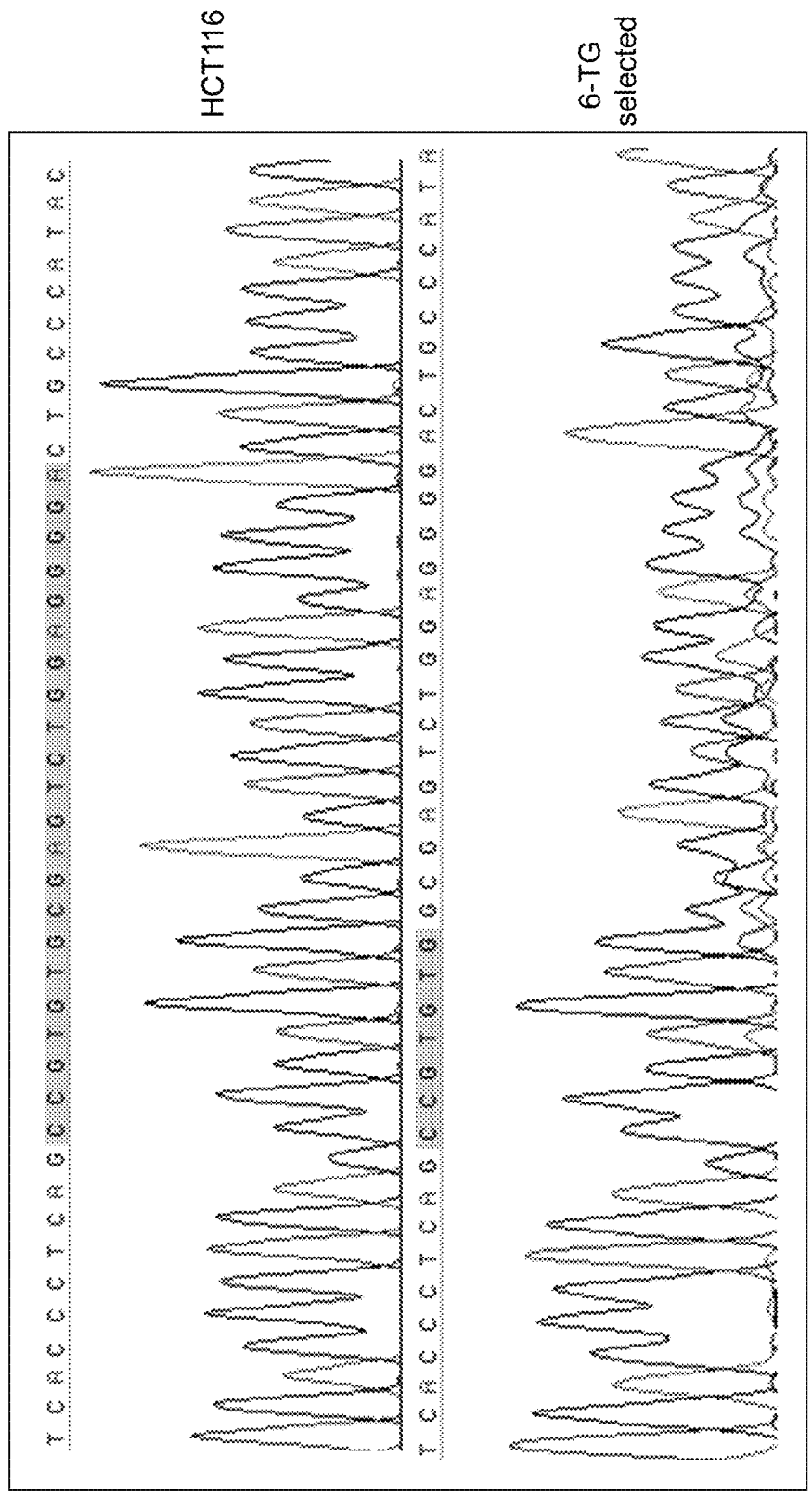
Figure 4:
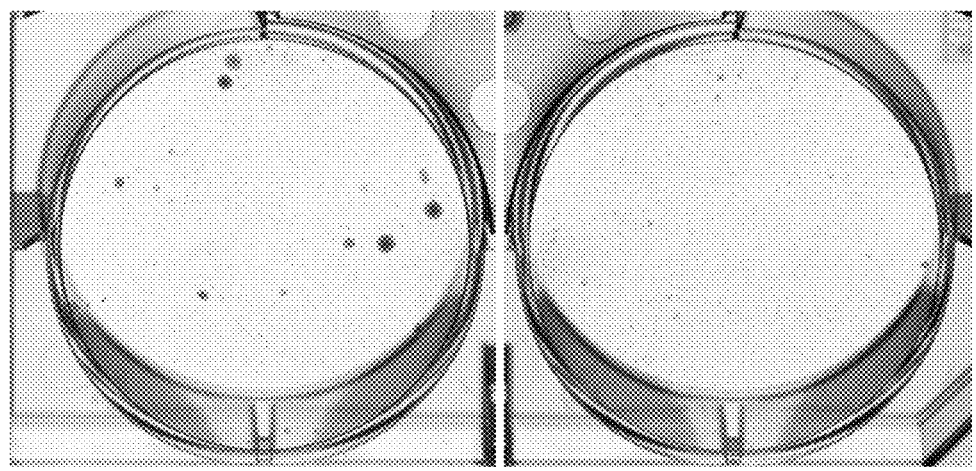
Figure 4:
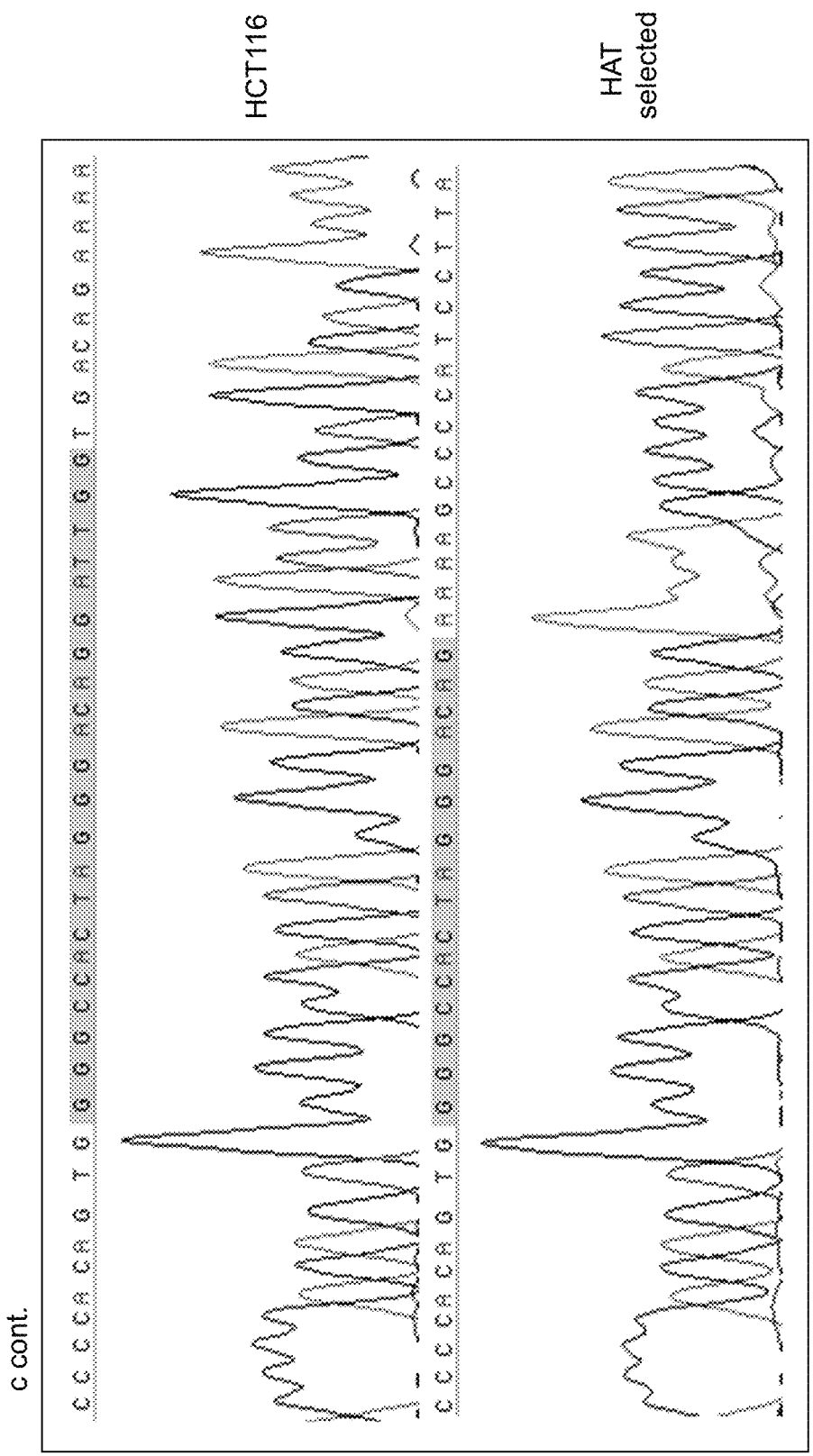

The 4-step cycle of HPRT disruption and correction can be used for iterative gene targeting. Both step 1 (disruption) and step 2 (correction) could be used for the enrichment of the co-targeted genes (see, FIG. 2, panels a through c). If step 3 (re-disruption) and step 4 (re-correction) were also used for co-targeting, one should be able to disrupt in an iterative way as many genes as cell viability permits (see, FIG. 4, panel a). To test this idea, the Exo1-cells obtained from the step 2 were transfected, co-targeting with plasmids expressing the HPRT gRNA2 and a gRNA against the Trex1 gene. The resulting 6-TG resistant cells were highly enriched for Trex1 mutations (see, FIG. 4, panel b).

These Exo 1-/Trex1-cells were then transfected with the HPRT-wt donor plasmid and the plasmids expressing the new editing gRNAs and a gRNA against the AAVS1 locus. The resulting HAT resistant cells were now highly enriched for mutations in the AAVS1 locus (see, FIG. 4, panel c).

Example 3: Editing of the PolQ Gene by Co-Editing the HPRT Gene

Figure 5:
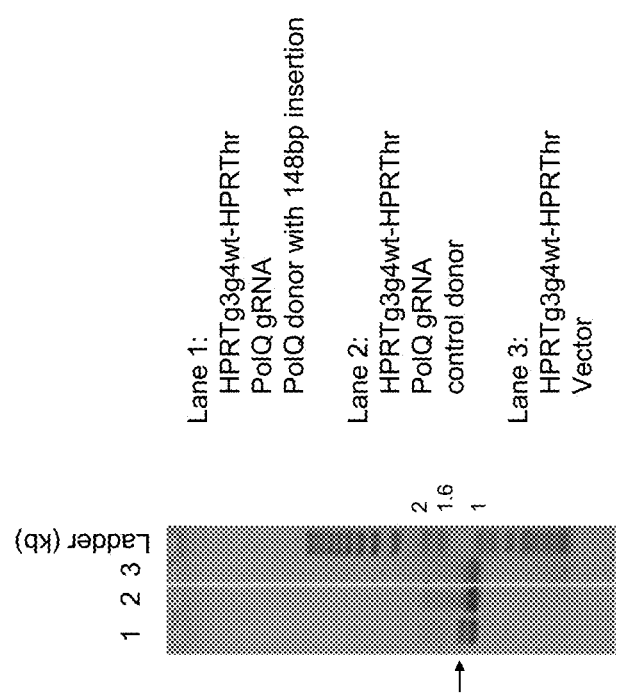
FIG. 5 shows enrichment of cells with PolQ gene editing by co-editing the HPRT gene.

A gRNA targeting the PolQ gene and a homologous donor were designed. These two plasmids were co-transfected with a plasmid that carries the two editing gRNAs and the donor sequence for the HPRT gene into the HPRT mutant HCT116 cells. A significant fraction of the resulting HAT resistant cells was found to carry the PolQ donor sequence, suggesting that co-editing the HPRT gene and PolQ gene occurred (see, FIG. 5). Referring to FIG. 5, a gRNA targeting the PolQ gene and a homologous PolQ donor were designed and subcloned into separate plasmids. The PolQ donor carries a 148 bp insertion at the gRNA target site (thus, can no longer by cut by Cas9). The PolQ gRNA and donor plasmids were co-transfected with the pHPRTg3g4 wt-HPRThr plasmid into Cas9-expressing HPRT mutant HCT116 cells. Four days later, cells were selected with HAT for 10 days. Genomic DNA was isolated from HAT resistant cells and the PolQ target region was amplified by PCR with two primers (outside of the donor) and analyzed by agarose gel electrophoresis. The slower migrating (longer) product (lane 1; indicated by arrow) is the expected size if the PolQ target is converted to the donor with the 148 bp insertion. This result shows that a significant fraction of the HPRT edited cells (HAT resistant) are also edited at the PolQ target region.

Example 4: Summary

These Examples describe an efficient enrichment method for iterative gene targeting. It is based on the principle that the HPRT gene can be both selected and counter-selected. The wild type HPRT gene is first disrupted by CRISPR-induced gene targeting and the resulting mutant cells are selected with 6-TG. The mutant HPRT gene is then corrected by CRISPR-induced gene editing and the resulting cells are selected with HAT. Homologous donors and gRNA are so designed that after two rounds of disruption/correction, the HPRT gene is edited back to the original wild type sequence, so the 4-step procedure can be repeated indefinitely. It was demonstrated that each step can be used to co-target another gene of interest, thus making it possible to sequentially disrupt as many genes as cell viability permits.

In principle, one could express multiple gRNAs to simultaneously disrupt multiple genes (multiplex CRISPR). However, the effectiveness of gRNAs can vary greatly, especially when competing for the same limited amount of Cas9. The isolation of a multi-mutant is thus far more difficult than that of a single mutant. In addition, single mutants are usually the ones first isolated and characterized. The iterative HPRT co-targeting thus provides a method complementary and often superior to multiplex CRISPR for the construction of mutants defective in multiple genes.

HPRT co-targeting uses an internal control for the competency of individual cells to execute CRISPR. 6-TG or HAT-resistant cells usually achieve 80-100% efficiency in co-targeting the gene of interest. It can also be used to evaluate the effectiveness of gRNAs and the essentiality of a gene. If similar numbers of 6-TG or HAT resistant cells are obtained, but there is no mutation in the co-targeted gene, one can confidently conclude that the gRNA is ineffective. On the other hand, if there are no or very few 6-TG or HAT resistant cells, the co-targeted gene is most likely essential.

The iterative HPRT co-targeting method uses only basic tissue culture setup and standard DNA transfection reagents. The method is demonstrated in HCT116 cells, but is expected to work in any cell that has a functional HPRT gene and can be selected by 6-TG and HAT.

Sequences:

(HPRTg3) (SEQ ID NO: 1)
AACATACAGAGAGACTACA (HPRTg4) (SEQ ID NO: 2)
TTAGAGAATATTTGTAGAG (HPRTg3-hr) (SEQ ID NO: 3)
ACAAAATGTGACATATACA (HPRTg4-hr) (SEQ ID NO: 4)
AATGGCTTATAATTGCGAG (HPRT) (SEQ ID NO: 5)
TGGGCAACAGAGCGAGATTC (HPRT) (SEQ ID NO: 6)
ATCAAAGTGGGAGGCCAGTG (Exo1) (SEQ ID NO: 7)
TCCAGTTCCAGCTGCCTAGA (Exo1) (SEQ ID NO: 8)
GTCTGCACATTCCTAGCCGA (AAVS1) (SEQ ID NO: 9)
ACAGGAGGTGGGGGTTAGAC (AAVS1) (SEQ ID NO: 10)
TATATTCCCAGGGCCGGTTA (Trex1) (SEQ ID NO: 11)
GCAGACCCTCATCTTTTTCG (for HPRT) (SEQ ID NO: 12)
GATGCTCACCTCTCCCACAC (for HPRT) (SEQ ID NO: 13)
ACATCCATGGGACTTCTGCC (for AAVS1) (SEQ ID NO: 14)
ACAGGAGGTGGGGGTTAGAC (for AAVS1) (SEQ ID NO: 15)
TATATTCCCAGGGCCGGTTA (for Trex1) (SEQ ID NO: 16)
GCAGACCCTCATCTTTTTCG (for Trex1) (SEQ ID NO: 17)
TACTGGGCTCAGATAGTTGAC (for Exo1) (SEQ ID NO: 18)
TCCAGTTCCAGCTGCCTAGA (for Exo1) (SEQ ID NO: 19)
GTCTGCACATTCCTAGCCGA pHPRTg2 (SEQ ID NO: 20):
AAATTGTAAGCGTTAATATTTTGTTAAAATTCGCGTTAAATTTTTGTTA
AATCAGCTCATTTTTTAACCAATAGGCCGAAATCGGCAAAATCCCTTAT
AAATCAAAAGAATAGACCGAGATAGGGTTGAGTGTTGTTCCAGTTTGGA
ACAAGAGTCCACTATTAAAGAACGTGGACTCCAACGTCAAAGGGCGAAA
AACCGTCTATCAGGGCGATGGCCCACTACGTGAACCATCACCCTAATCA
AGTTTTTTGGGGTCGAGGTGCCGTAAAGCACTAAATCGGAACCCTAAAG
GGAGCCCCGATTTAGAGCTTGACGGGGAAAGCCGGCGAACGTGGCGAG
AAAGGAAGGGAAGAAAGCGAAAGGAGCGGGCGCTAGGGCGCTGGCAAGT
GTAGCGGTCACGCTGCGCGTAACCACCACACCCGCCGCGCTTAATGCGC
CGCTACAGGGCGCGTCAGGTGGCACTTTTCGGGGAAATGTGCGCGGAAC
CCCTATTTGTTTATTTTTCTAAATACATTCAAATATGTATCCGCTCATG
AGACAATAACCCTGATAAATGCTTCAATAATATTGAAAAAGGAAGAGTC
CTGAGGCGGAAAGAACCAGCTGTGGAATGTGTGTCAGTTAGGGTGTGGA
AAGTCCCCAGGCTCCCCAGCAGGCAGAAGTATGCAAAGCATGCATCTCA
ATTAGTCAGCAACCAGGTGTGGAAAGTCCCCAGGCTCCCCAGCAGGCAG
AAGTATGCAAAGCATGCATCTCAATTAGTCAGCAACCATAGTCCCGCCC
CTAACTCCGCCCATCCCGCCCCTAACTCCGCCCAGTTCCGCCCATTCTC
CGCCCCATGGCTGACTAATTTTTTTATTTATGCAGAGGCCGAGGCCGC
CTCGGCCTCTGAGCTATTCCAGAAGTAGTGAGGAGGCTTTTTTGGAGGC
CTAGGCTTTTGCAAAGATCGATCAAGAGACAGGATGAGGATCGTTTCGC
ATGATTGAACAAGATGGATTGCACGCAGGTTCTCCGGCCGCTTGGGTGG
AGAGGCTATTCGGCTATGACTGGGCACAACAGACAATCGGCTGCTCTGA
TGCCGCCGTGTTCCGGCTGTCAGCGCAGGGGCGCCCGGTTCTTTTTGTC
AAGACCGACCTGTCCGGTGCCCTGAATGAACTGCAAGACGAGGCAGCGC
GGCTATCGTGGCTGGCCACGACGGGCGTTCCTTGCGCAGCTGTGCTCGA
CGTTGTCACTGAAGCGGGAAGGGACTGGCTGCTATTGGGCGAAGTGCCG
GGGCAGGATCTCCTGTCATCTCACCTTGCTCCTGCCGAGAAAGTATCCA
TCATGGCTGATGCAATGCGGCGGCTGCATACGCTTGATCCGGCTACCTG
CCCATTCGACCACCAAGCGAAACATCGCATCGAGCGAGCACGTACTCGG
ATGGAAGCCGGTCTTGTCGATCAGGATGATCTGGACGAGGAACATCAGG
GGCTCGCGCCAGCCGAACTGTTCGCCAGGCTCAAGGCGAGCATGCCCGA
CGGCGAGGATCTCGTCGTGACCCATGGCGATGCCTGCTTGCCGAATATC
ATGGTGGAAAATGGCCGCTTTTCTGGATTCATCGACTGTGGCCGGCTGG
GTGTGGCGGACCGCTATCAGGACATAGCGTTGGCTACCCGTGATATTGC
TGAGGAACTTGGCGGCGAATGGGCTGACCGCTTCCTCGTGCTTTACGGT
ATCGCCGCTCCCGATTCGCAGCGCATCGCCTTCTATCGCCTTCTTGACG
AGTTCTTCTGAGCGGGACTCTGGGGTTCGAAATGACCGACCAAGCGACG
CCCAACCTGCCATCACGAGATTTCGATTCCACCGCCGCCTTCTATGAAA
GGTTGGGCTTCGGAATCGTTTTCCGGGACGCCGGCTGGATGATCCTCCA
GCGCGGGGATCTCATGCTGGAGTTCTTCGCCCACCCTAGGGGGAGGCTA ACTGAAACACGGAAGGAGACAATACCGGAAGGAACCCGCGCTATGACGG
CAATAAAAAGACAGAATAAAACGCACGGTGTTGGGTCGTTTGTTCATAA
ACGCGGGGTTCGGTCCCAGGGCTGGCACTCTGTCGATACCCCACCGAGA
CCCCATTGGGGCCAATACGCCCGCGTTTCTTCCTTTTCCCCACCCCACC
CCCCAAGTTCGGGTGAAGGCCCAGGGCTCGCAGCCAACGTCGGGGCGGC
AGGCCCTGCCATAGCCTCAGGTTACTCATATATACTTTAGATTGATTTA
AAACTTCATTTTTAATTTAAAAGGATCTAGGTGAAGATCCTTTTTGATA
ATCTCATGACCAAAATCCCTTAACGTGAGTTTTCGTTCCACTGAGCGTC
AGACCCCGTAGAAAAGATCAAAGGATCTTCTTGAGATCCTTTTTTTCTG
CGCGTAATCTGCTGCTTGCAAACAAAAAAACCACCGCTACCAGCGGTGG
TTTGTTTGCCGGATCAAGAGCTACCAACTCTTTTTCCGAAGGTAACTGG
CTTCAGCAGAGCGCAGATACCAAATACTGTCCTTCTAGTGTAGCCGTAG
TTAGGCCACCACTTCAAGAACTCTGTAGCACCGCCTACATACCTCGCTC
TGCTAATCCTGTTACCAGTGGCTGCTGCCAGTGGCGATAAGTCGTGTCT
TACCGGGTTGGACTCAAGACGATAGTTACCGGATAAGGCGCAGCGGTCG
GGCTGAACGGGGGGTTCGTGCACACAGCCCAGCTTGGAGCGAACGACCT
ACACCGAACTGAGATACCTACAGCGTGAGCTATGAGAAAGCGCCACGCT
TCCCGAAGGGAGAAAGGCGGACAGGTATCCGGTAAGCGGCAGGGTCGGA
ACAGGAGAGCGCACGAGGGAGCTTCCAGGGGGAAACGCCTGGTATCTTT
ATAGTCCTGTCGGGTTTCGCCACCTCTGACTTGAGCGTCGATTTTTGTG
ATGCTCGTCAGGGGGGCGGAGCCTATGGAAAAACGCCAGCAACGCGGCC
TTTTTACGGTTCCTGGCCTTTTGCTGGCCTTTTGCTCACATGTTGTGCT
AGCATTCGCGAATTCCATTCAGGCTGCGCAACTGTTGGGAAGGGCGATC
GGTGCGGGCCTCTTCGCTATTACGCCAGCTGGCGAAAGGGGGATGTGCT
GCAAGGCGATTAAGTTGGGTAACGCCAGGGTTTTCCCAGTCACGACGTT
GTAAAACGACGGCCAGTTAGAACTAGTTGTACAAAAAAGCAGGCTTTAA
AGGAACCAATTCAGTCGACTGGATCCGGTACCAAGGTCGGGCAGGAAGA
GGGCCTATTTCCCATGATTCCTTCATATTTGCATATACGATACAAGGCT
GTTAGAGAGATAATTAGAATTAATTTGACTGTAAACACAAAGATATTAG
TACAAAATACGTGACGTAGAAAGTAATAATTTCTTGGGTAGTTTGCAGT
TTTAAAATTATGTTTTAAAATGGACTATCATATGCTTACCGTAACTTGA
AAGTATTTCGATTTCTTGGCTTTATATATCTTGTGGAAAGGACGAAACA
CCGAAGTAATTCACTTACAGTCGTTTTAGAGCTAGAAATAGCAAGTTAA
AATAAGGCTAGTCCGTTATCAACTTGAAAAAGTGGCACCGAGTCGGTGC
TTTTTTCTAGACCCAGCTTTCTTGTACAAAGTTGGCATTACAATTGGA
TATCACGCGT pHPRTg3g4wt-HPRThr (SEQ ID NO: 21)
AAATTGTAAGCGTTAATATTTTGTTAAAATTCGCGTTAAATTTTTGTTA
AATCAGCTCATTTTTTAACCAATAGGCCGAAATCGGCAAAATCCCTTAT
AAATCAAAAGAATAGACCGAGATAGGGTTGAGTGTTGTTCCAGTTTGGA
ACAAGAGTCCACTATTAAAGAACGTGGACTCCAACGTCAAAGGGCGAAA

```
AACCGTCTATCAGGGCGATGGCCCACTACGTGAACCATCACCCTAATCA
AGTTTTTTGGGGTCGAGGTGCCGTAAAGCACTAAATCGGAACCCTAAAG
GGAGCCCCCGATTTAGAGCTTGACGGGGAAAGCCGGCGAACGTGGCGAG
AAAGGAAGGGAAGAAAGCGAAAGGAGCGGGCGCTAGGGCGCTGGCAAGT
GTAGCGGTCACGCTGCGCGTAACCACCACACCCGCCGCGCTTAATGCGC
CGCTACAGGGCGCGTCAGGTGGCACTTTTCGGGGAAATGTGCGCGGAAC
CCCTATTTGTTTATTTTTCTAAATACATTCAAATATGTATCCGCTCATG
AGACAATAACCCTGATAAATGCTTCAATAATATTGAAAAAGGAAGAGTC
CTGAGCGGAAAGAACCAGCTGTGGAATGTGTGTCAGTTAGGGTGTGGAA
AGTCCCCAGGCTCCCCAGCAGGCAGAAGTATGCAAAGCATGCATCTCAA
TTAGTCAGCAACCAGGTGTGGAAAGTCCCCAGGCTCCCCAGCAGGCAGA
AGTATGCAAAGCATGCATCTCAATTAGTCAGCAACCATAGTCCCGCCCC
TAACTCCGCCCATCCCGCCCCTAACTCCGCCCAGTTCCGCCCATTCTCC
GCCCCATGGCTGACTAATTTTTTTATTTATGCAGAGGCCGAGGCCGCC
TCGGCCTCTGAGCTATTCCAGAAGTAGTGAGGAGGCTTTTTTGGAGGCC
TAGGCTTTTGCAAAGATCGATCAAGAGACAGGATGAGGATCGTTTCGCA
TGATTGAACAAGATGGATTGCACGCAGGTTCTCCGGCCGCTTGGGTGGA
GAGGCTATTCGGCTATGACTGGGCACAACAGACAATCGGCTGCTCTGAT
GCCGCCGTGTTCCGGCTGTCAGCGCAGGGGCGCCCGGTTCTTTTTGTCA
AGACCGACCTGTCCGGTGCCCTGAATGAACTGCAAGACGAGGCAGCGCG
GCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGG
GGCAGGATCTCCTGTCATCTCACCTTGCTCCTGCCGAGAAAGTATCCAT
CATGGCTGATGCAATGCGGCGGCTGCATACGCTTGATCCGGCTACCTGC
CCATTCGACCACCAAGCGAAACATCGCATCGAGCGAGCACGTACTCGGA
TGGAAGCCGGTCTTGTCGATCAGGATGATCTGGACGAGGAACATCAGGG
GCTCGCGCCAGCCGAACTGTTCGCCAGGCTCAAGGCGAGCATGCCCGAC
GGCGAGGATCTCGTCGTGACCCATGGCGATGCCTGCTTGCCGAATATCA
TGGTGGAAAATGGCCGCTTTTCTGGATTCATCGACTGTGGCCGGCTGGG
TGTGGCGGACCGCTATCAGGACATAGCGTTGGCTACCCGTGATATTGCT
GAGGAACTTGGCGGCGAATGGGCTGACCGCTTCCTCGTGCTTTACGGTA
TCGCCGCTCCCGATTCGCAGCGCATCGCCTTCTATCGCCTTCTTGACGA
GTTCTTCTGAGCGGGACTCTGGGGTTCGAAATGACCGACCAAGCGACGC
CCAACCTGCCATCACGAGATTTCGATTCCACCGCCGCCTTCTATGAAAG
GTTGGGCTTCGGAATCGTTTTCCGGGACGCCGGCTGGATGATCCTCCAG
CGCGGGGATCTCATGCTGGAGTTCTTCGCCCACCCTAGGGGGAGGCTAA
CTGAAACACGGAAGGAGACAATACCGGAAGGAACCCGCGCTATGACGGC
AATAAAAAGACAGAATAAAACGCACGGTGTTGGGTCGTTTGTTCATAAA
CGCGGGGTTCGGTCCCAGGGCTGGCACTCTGTCGATACCCCACCGAGAC
CCCATTGGGGCCAATACGCCCGCGTTTCTTCCTTTTCCCCACCCCACCC
CCCAAGTTCGGGTGAAGGCCCAGGGCTCGCAGCCAACGTCGGGGCGGCA
GGCCCTGCCATAGCCTCAGGTTACTCATATATACTTTAGATTGATTTAA
AACTTCATTTTTAATTTAAAAGGATCTAGGTGAAGATCCTTTTTGATAA
TCTCATGACCAAAATCCCTTAACGTGAGTTTTCGTTCCACTGAGCGTCA
GACCCCGTAGAAAAGATCAAAGGATCTTCTTGAGATCCTTTTTTTCTGC
GCGTAATCTGCTGCTTGCAAACAAAAAAACCACCGCTACCAGCGGTGGT
TTGTTTGCCGGATCAAGAGCTACCAACTCTTTTTCCGAAGGTAACTGGC
TTCAGCAGAGCGCAGATACCAAATACTGTCCTTCTAGTGTAGCCGTAGT
TAGGCCACCACTTCAAGAACTCTGTAGCACCGCCTACATACCTCGCTCT
GCTAATCCTGTTACCAGTGGCTGCTGCCAGTGGCGATAAGTCGTGTCTT
ACCGGGTTGGACTCAAGACGATAGTTACCGGATAAGGCGCAGCGGTCGG
GCTGAACGGGGGGTTCGTGCACACAGCCCAGCTTGGAGCGAACGACCTA
CACCGAACTGAGATACCTACAGCGTGAGCTATGAGAAAGCGCCACGCTT
CCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGA
TGCTCGTCAGGGGGCGGAGCCTATGGAAAAACGCCAGCAACGCGGCCT
TTTTACGGTTCCTGGCCTTTTGCTGGCCTTTTGCTCACATGTTGTGCTA
GTTGTACAAAAAAGCAGGCTTTAAAGGAACCAATTCAGTCGACTGGATC
CGGTACCAAGGTCGGGCAGGAAGAGGGCCTATTTCCCATGATTCCTTCA
TATTTGCATATACGATACAAGGCTGTTAGAGAGATAATTAGAATTAATT
TGACTGTAAACACAAAGATATTAGTACAAAATACGTGACGTAGAAAGTA
ATAATTTCTTGGGTAGTTTGCAGTTTTAAAATTATGTTTTAAAATGGAC
TATCATATGCTTACCGTAACTTGAAAGTATTTCGATTTCTTGGCTTTAT
ATATCTTGTGGAAAGGACGAAACACCGAACATACAGAGAGACTACAGTT
TTAGAGCTAGAAATAGCAAGTTAAAATAAGGCTAGTCCGTTATCAACTT
GAAAAAGTGGCACCGAGTCGGTGCTTTTTTTCTAGACCCAGCTTTCTTG
TACAAAGTTGGCATTACAATTCCATTCAGGCTGCGCAACTGTTGGGAAG
GGCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTCA
CGACGTTGTAAAACGACGGCCAGTTAGAACTAGTTGTACAAAAAAGCAG
GCTTTAAAGGAACCAATTCAGTCGACTGGATCCGGTACCAAGGTCGGGC
AGGAAGAGGGCCTATTTCCCATGATTCCTTCATATTTGCATATACGATA
CAAGGCTGTTAGAGAGATAATTAGAATTAATTTGACTGTAAACACAAAG
ATATTAGTACAAAATACGTGACGTAGAAAGTAATAATTTCTTGGGTAGT
TTGCAGTTTTAAAATTATGTTTTAAAATGGACTATCATATGCTTACCGT
AACTTGAAAGTATTTCGATTTCTTGGCTTTATATATCTTGTGGAAAGGA
CGAAACACCGTTAGAGAATATTTGTAGAGGTTTTAGAGCTAGAAATAGC
AAGTTAAAATAAGGCTAGTCCGTTATCAACTTGAAAAAGTGGCACCGAG
TCGGTGCTTTTTTTCTAGACCCAGCTTTCTTGTACAAAGTTGGCATTAC
AATTGGATAATTCGAGCTCGGTACCCACATTTATCATCTGAAATAATAA
```

-continued
TGCAACAATTATTGTATATTAAAGCTGTTCAACTATTTCAGCCAACAAG
AAGTGTCACCCTAGCCTGGCCAGGTTCCAGTTCTAAGGACGTCTGTACT
AGACTACAGCTTTATGTGACTAATGGGAACCATCAGTCTGTTCAAATTA
TGAGGTGCTGGAAGGAGAAAACAATTCTCTTTCCTAAATTTTTATGCGT
GTTTTGAAAAATGAGTGAGAAAAGAAGCAATTACTTACATTCAAATCC
CTGAAGTATTCATTATAGTCAAGGGCATATCCTACAACAAACTTGTCTG
GAATTTCAAATCCAACAACTAAAAAGAATCATAATTCATCATTTAGATA
AAGAAAACATCACTTTTAAATCTAATACTGGCAAATGTGCCTCTCGCAA
TTATAAGCCATTTCACATAAAACTCTTTTAGGTTAAAGATGGTTAAATG
ATTGACAAAAAAGTAATTCACTTACAGTCTGGCTTATATCCAACAGAC
CGCGGGGTCCTTTTCACCAGCAAGCTGTTAATTACAAAATGTGACATAT
ACAGGGCATTACAAAAGAGAAGACTGACGTTTCTAAACACTGTTTCATT
TCATCCGTGCTGAGTGTACCATGGTCACTTTTAACACACCCAAGGAAAG
ACTATGAAATGGAGAGCTAAATTATGGGGATTACTAGGAAGGGGCAGCA
ATGAGTTGACACTACAGACAAGGCACTTGGTTGATCACCTGGAACCTGA
AGGACAGTTCTGAGACCTGCACCCTGACTACCCATGTGTCCATTGAAGG
GGAGCTAATAAGGAGGATTAATGGGTACAGAGTGTCAATGAGCAAAGAT
GAAAAGGGCTCTCAGTCTAGAAAACCTTGGAAATACAATCCCTAAACTAT
AAAAGGGTGTGGGAGGTGAGCATCACCTTTTATCACAACAGGGACCT
GCAGCCATGCATGCCATGGCCACCACGCGT pHPRTg3g4hr-HPRTwt (SEQ ID NO: 22):
AAATTGTAAGCGTTAATATTTTGTTAAAATTCGCGTTAAATTTTGTTA
AATCAGCTCATTTTTTAACCAATAGGCCGAAATCGGCAAAATCCCTTAT
AAATCAAAGAAAGACCGAGATAGGGTTGAGTGTTGTTCCAGTTTGGAA
CAAGAGTCCACTATTAAAGAACGTGGACTCCAACGTCAAAGGGCGAAAA
ACCGTCTATCAGGGCGATGGCCCACTACGTGAACCATCACCCTAATCAA
GTTTTTTGGGGTCGAGGTGCCGTAAAGCACTAAATCGGAACCCTAAAGG
GAGCCCCCGATTTAGAGCTTGACGGGGAAAGCCGGCGAACGTGGCGAGA
AAGGAAGGGAAGAAAGCGAAAGGAGCGGGCGCTAGGGCGCTGGCAAGTG
TAGCGGTCACGCTGCGCGTAACCACCACACCCGCCGCGCTTAATGCGCC
GCTACAGGGCGCGTCAGGTGGCACTTTTCGGGGAAATGTGCGCGGAACC
CCTATTTGTTTATTTTTCTAAATACATTCAAATATGTATCCGCTCATGA
GACAATAACCCTGATAAATGCTTCAATAATATTGAAAAAGGAAGAGTCC
TGAGGCGGAAAGAACCAGCTGTGGAATGTGTGTCAGTTAGGGTGTGGAA
AGTCCCCAGGCTCCCCAGCAGGCAGAAGTATGCAAAGCATGCATCTCAA
TTAGTCAGCAACCAGGTGTGGAAAGTCCCCAGGCTCCCCAGCAGGCAGA
AGTATGCAAAGCATGCATCTCAATTAGTCAGCAACCATAGTCCCGCCCC
TAACTCCGCCCATCCCGCCCCTAACTCCGCCCAGTTCCGCCCATTCTCC
GCCCCATGGCTGACTAATTTTTTTATTTATGCAGAGGCCGAGGCCGCC
TCGGCCTCTGAGCTATTCCAGAAGTAGTGAGGAGGCTTTTTTGGAGGCC
TAGGCTTTTGCAAAGATCGATCAAGAGACAGGATGAGGATCGTTTCGCA -continued
TGATTGAACAAGATGGATTGCACGCAGGTTCTCCGGCCGCTTGGGTGGA
GAGGCTATTCGGCTATGACTGGGCACAACAGACAATCGGCTGCTCTGAT
GCCGCCGTGTTCCGGCTGTCAGCGCAGGGGCGCCCGGTTCTTTTTGTCA
AGACCGACCTGTCCGGTGCCCTGAATGAACTGCAAGACGAGGCAGCGCG
GCTATCGTGGCTGGCCACGACGGGCGTTCCTTGCGCAGCTGTGCTCGAC
GTTGTCACTGAAGCGGGAAGGGACTGGCTGCTATTGGGCGAAGTGCCGG
GGCAGGATCTCCTGTCATCTCACCTTGCTCCTGCCGAGAAAGTATCCAT
CATGGCTGATGCAATGCGGCGGCTGCATACGCTTGATCCGGCTACCTGC
CCATTCGACCACCAAGCGAAACATCGCATCGAGCGAGCACGTACTCGGA
TGGAAGCCGGTCTTGTCGATCAGGATGATCTGGACGAGGAACATCAGGG
GCTCGCGCCAGCCGAACTGTTCGCCAGGCTCAAGGCGAGCATGCCCGAC
GGCGAGGATCTCGTCGTGACCCATGGCGATGCCTGCTTGCCGAATATCA
TGGTGGAAAATGGCCGCTTTTCTGGATTCATCGACTGTGGCCGGCTGGG
TGTGGCGGACCGCTATCAGGACATAGCGTTGGCTACCCGTGATATTGCT
GAGGAACTTGGCGGCGAATGGGCTGACCGCTTCCTCGTGCTTTACGGTA
TCGCCGCTCCCGATTCGCAGCGCATCGCCTTCTATCGCCTTCTTGACGA
GTTCTTCTGAGCGGGACTCTGGGGTTCGAAATGACCGACCAAGCGACGC
CCAACCTGCCATCACGAGATTTCGATTCCACCGCCGCCTTCTATGAAAG
GTTGGGCTTCGGAATCGTTTTCCGGGACGCCGGCTGGATGATCCTCCAG
CGCGGGGATCTCATGCTGGAGTTCTTCGCCCACCCTAGGGGGAGGCTAA
CTGAAACACGGAAGGAGACAATACCGGAAGGAACCCGCGCTATGACGG
AATAAAAAGACAGAATAAAACGCACGGTGTTGGGTCGTTTGTTCATAAA
CGCGGGGTTCGGTCCCAGGGCTGGCACTCTGTCGATACCCCACCGAGAC
CCCATTGGGGCCAATACGCCCGCGTTTCTTCCTTTTCCCCACCCCACCC
CCCAAGTTCGGGTGAAGGCCCAGGGCTCGCAGCCAACGTCGGGGCGGCA
GGCCCTGCCATAGCCTCAGGTTACTCATATATACTTTAGATTGATTTAA
AACTTCATTTTTAATTTAAAAGGATCTAGGTGAAGATCCTTTTTGATAA
TCTCATGACCAAAATCCCTTAACGTGAGTTTTCGTTCCACTGAGCGTCA
GACCCCGTAGAAAAGATCAAAGGATCTTCTTGAGATCCTTTTTTTCTGC
GCGTAATCTGCTGCTTGCAAACAAAAAAACCACCGCTACCAGCGGTGGT
TTGTTTGCCGGATCAAGAGCTACCAACTCTTTTTCCGAAGGTAACTGGC
TTCAGCAGAGCGCAGATACCAAATACTGTCCTTCTAGTGTAGCCGTAGT
TAGGCCACCACTTCAAGAACTCTGTAGCACCGCCTACATACCTCGCTCT
GCTAATCCTGTTACCAGTGGCTGCTGCCAGTGGCGATAAGTCGTGTCTT
ACCGGGTTGGACTCAAGACGATAGTTACCGGATAAGGCGCAGCGGTCGG
GCTGAACGGGGGGTTCGTGCACACAGCCCAGCTTGGAGCGAACGACCTA
CACCGAACTGAGATACCTACAGCGTGAGCTATGAGAAAGCGCCACGCTT
CCCGAAGGGAGAAAGGCGGACAGGTATCCGGTAAGCGGCAGGGTCGGAA
CAGGAGAGCGCACGAGGGAGCTTCCAGGGGGAAACGCCTGGTATCTTTA
TAGTCCTGTCGGGTTTCGCCACCTCTGACTTGAGCGTCGATTTTTGTGA
TGCTCGTCAGGGGGCGGAGCCTATGGAAAAACGCCAGCAACGCGGCCT TTTTACGGTTCCTGGCCTTTTGCTGGCCTTTTGCTCACATGTTGTGCTA
GTTGTACAAAAAAGCAGGCTTTAAAGGAACCAATTCAGTCGACTGGATC
CGGTACCAAGGTCGGGCAGGAAGAGGGCCTATTTCCCATGATTCCTTCA
TATTTGCATATACGATACAAGGCTGTTAGAGAGATAATTAGAATTAATT
TGACTGTAAACACAAAGATATTAGTACAAAATACGTGACGTAGAAAGTA
ATAATTTCTTGGGTAGTTTGCAGTTTTAAAATTATGTTTTAAATGGAC
TATCATATGCTTACCGTAACTTGAAAGTATTTCGATTTCTTGGCTTTAT
ATATCTTGTGGAAAGGACGAAACACCGACAAAATGTGACATATACAGTT
TTAGAGCTAGAAATAGCAAGTTAAAATAAGGCTAGTCCGTTATCAACTT
GAAAAAGTGGCACCGAGTCGGTGCTTTTTTTCTAGACCCAGCTTTCTTG
TACAAAGTTGGCATTACAATTCCATTCAGGCTGCGCAACTGTTGGGAAG
GGCGATCGGTGCGGGCCTCTTCGCTATTACGCCAGCTGGCGAAAGGGGG
ATGTGCTGCAAGGCGATTAAGTTGGGTAACGCCAGGGTTTTCCCAGTCA
CGACGTTGTAAAACGACGGCCAGTTAGAACTAGTTGTACAAAAAAGCAG
GCTTTAAAGGAACCAATTCAGTCGACTGGATCCGGTACCAAGGTCGGGC
AGGAAGAGGGCCTATTTCCCATGATTCCTTCATATTTGCATATACGATA
CAAGGCTGTTAGAGAGATAATTAGAATTAATTTGACTGTAAACACAAAG
ATATTAGTACAAAATACGTGACGTAGAAAGTAATAATTTCTTGGGTAGT
TTGCAGTTTTAAAATTATGTTTTAAAATGGACTATCATATGCTTACCGT
AACTTGAAAGTATTTCGATTTCTTGGCTTTATATATCTTGTGGAAAGGA
CGAAACACCGAATGGCTTATAATTGCGAGGTTTTAGAGCTAGAAATAGC
AAGTTAAAATAAGGCTAGTCCGTTATCAACTTGAAAAAGTGGCACCGAG
TCGGTGCTTTTTTTCTAGACCCAGCTTTCTTGTACAAAGTTGGCATTAC
AATTCGAGCTCGGTACCCGGGGATCCTCTAGAGTCGATGCTCACCTCTC
CCACACCCTTTTATAGTTTAGGGATTGTATTTCCAAGGTTTCTAGACTG
AGAGCCCTTTTCATCTTTGCTCATTGACACTCTGTACCCATTAATCCTC
CTTATTAGCTCCCCTTCAATGGACACATGGGTAGTCAGGGTGCAGGTCT
CAGAACTGTCCTTCAGGTTCCAGGTGATCAACCAAGTGCCTTGTCTGTA
GTGTCAACTCATTGCTGCCCCTTCCTAGTAATCCCCATAATTTAGCTCT
CCATTTCATAGTCTTTCCTTGGGTGTGTTAAAAGTGACCATGGTACACT
CAGCACGGATGAAATGAAACAGTGTTTAGAAACGTCAGTCTTCTCTTTT
GTAATGCCCTGTAGTCTCTCTGTATGTTATATGTCACATTTTGTAATTA
ACAGCTTGCTGGTGAAAAGGACCCCACGAAGTGTTGGATATAAGCCAGA
CTGTAAGTGAATTACTTTTTTTGTCAATCATTTAACCATCTTTAACCTA
AAAGAGTTTATGTGAAATGGCTTATAATTGCTTAGAGAATATTTGTAG
AGAGGCACATTTGCCAGTATTAGATTTAAAAGTGATGTTTTCTTTATCT
AAATGATGAATTATGATTCTTTTTAGTTGTTGGATTTGAAATTCCGAC
AAGTTTGTTGTAGGATATGCCCTTGACTATAATGAATACTTCAGGGATT
TGAATGTAAGTAATTGCTTCTTTTTTCTCACTCATTTTTCAAAACACGCA
TAAAAATTTAGGAAAGAGAATTGTTTTCTCCTTCCAGCACCTCATAATT TGAACAGACTGATGGTTCCCATTAGTCACATAAAGCTGTAGTCTAGTAC
AGACGTCCTTAGAACTGGAACCTGGCCAGGCTAGGGTGACACTTCTTGT
TGGCTGAAATAGTTGAACAGCTTTAATATACAATAATTGTTGCATTATT
ATTTCAGATGATAAATGTGGTCATAAGTAAGAAATAAATGATCGAGTTT
AGTCTTTTAATTCACTGTCCTTTGAATACCTGCCTCTTACTCTGGAGGC
AGAAGTCCCATGGATGTGACCTGCAGCCATGCATGCCATGGCCACCACG
CGT HPRT-hr template (SEQ ID NO: 23):
GGTACCCACATTTATCATCTGAAATAATAATGCAACAATTATTGTATAT
TAAAGCTGTTCAACTATTTCAGCCAACAAGAAGTGTCACCCTAGCCTGG
CCAGGTTCCAGTTCTAAGGACGTCTGTACTAGACTACAGCTTTATGTGA
CTAATGGGAACCATCAGTCTGTTCAAATTATGAGGTGCTGGAAGGAGAA
AACAATTCTCTTTCCTAAATTTTTATGCGTGTTTTGAAAAATGAGTGAG
AAAAAGAAGCAATTACTTACATTCAAATCCCTGAAGTATTCATTATAGT
CAAGGGCATATCCTACAACAAACTTGTCTGGAATTTCAAATCCAACAAC
TAAAAGAATCATAATTCATCATTTAGATAAAGAAAACATCACTTTTAA
ATCTAATACTGGCAAATGTGCCTCTCGCAATTATAAGCCATTTCACATA
AAACTCTTTTAGGTTAAAGATGGTTAAATGATTGACAAAAAAGTAATT
CACTTACAGTCTGGCTTATATCCAACAGACCGCGGGGTCCTTTTCACCA
GCAAGCTGTTAATTACAAAATGTGACATATACAGGGCATTACAAAAGAG
AAGACTGACGTTTCTAAACACTGTTTCATTTCATCCGTGCTGAGTGTAC
CATGGTCACTTTTAACACACCCAAGGAAAGACTATGAAATGGAGAGCTA
AATTATGGGGATTACTAGGAAGGGGCAGCAATGAGTTGACACTACAGAC
AAGGCACTTGGTTGATCACCTGGAACCTGAAGGACAGTTCTGAGACCTG
CACCCTGACTACCCATGTGTCCATTGAAGGGGAGCTAATAAGGAGGATT
AATGGGTACAGAGTGTCAATGAGCAAAGATGAAAAGGGCTCTCAGTCTA
GAAACCTTGGAAATACAATCCCTAAACTATAAAAGGGTGTGGGAGAGGT
GAGCATCACCTTTTATCACAACAGG HPRT-wt template (SEQ ID NO: 24):
GATGCTCACCTCTCCCACACCCTTTTATAGTTTAGGGATTGTATTTCCA
AGGTTTCTAGACTGAGAGCCCTTTTCATCTTTGCTCATTGACACTCTGT
ACCCATTAATCCTCCTTATTAGCTCCCCTTCAATGGACACATGGGTAGT
CAGGGTGCAGGTCTCAGAACTGTCCTTCAGGTTCCAGGTGATCAACCAA
GTGCCTTGTCTGTAGTGTCAACTCATTGCTGCCCCTTCCTAGTAATCCC
CATAATTTAGCTCTCCATTTCATAGTCTTTCCTTGGGTGTGTTAAAAGT
GACCATGGTACACTCAGCACGGATGAAATGAAACAGTGTTTAGAAACGT
CAGTCTTCTCTTTTGTAATGCCCTGTAGTCTCTCTGTATGTTATATGTC
ACATTTTGTAATTAACAGCTTGCTGGTGAAAAGGACCCCACGAAGTGTT
GGATATAAGCCAGACTGTAAGTGAATTACTTTTTTTGTCAATCATTTAA
CCATCTTTAACCTAAAAGAGTTTATGTGAAATGGCTTATAATTGCTTA
GAGAATATTTGTAGAGAGGCACATTTGCCAGTATTAGATTTAAAAGTGA
TGTTTTCTTTATCTAAATGATGAATTATGATTCTTTTTAGTTGTTGGAT -continued

TTGAAATTCCAGACAAGTTTGTTGTAGGATATGCCCTTGACTATAATGA

ATACTTCAGGGATTTGAATGTAAGTAATTGCTTCTTTTTCTCACTCATT

TTTCAAAACACGCATAAAAATTTAGGAAAGAGAATTGTTTTCTCCTTCC

AGCACCTCATAATTTGAACAGACTGATGGTTCCCATTAGTCACATAAAG

CTGTAGTCTAGTACAGACGTCCTTAGAACTGGAACCTGGCCAGGCTAGG

GTGACACTTCTTGTTGGCTGAAATAGTTGAACAGCTTTAATATACAATA

ATTGTTGCATTATTATTTCAGATGATAAATGTGGTCATAAGTAAGAAAT

AAATGATCGAGTTTAGTCTTTTAATTCACTGTCCTTTGAATACCTGCCT

CTTACTCTGGAGGCAGAAGTCCCATGGATGT

HPRT gRNA g2 (SEQ ID NO: 25):
AAGTAATTCACTTACAGTC

The present disclosure is not limited to the embodiments described and exemplified above, but is capable of variation and modification within the scope of the appended claims.

What is claimed is:

1. A method comprising:
   a) providing a Cas9-competent cell comprising a hypoxanthine guanine phosphoribosyl transferase (HPRT) gene comprising an alteration;
   b) co-transfecting the cell with a guide RNA (gRNA) that hybridizes to a nucleic acid sequence of a target gene, a first gRNA that hybridizes to the HPRT gene upstream of the alteration, a second gRNA that hybridizes to the HPRT gene downstream of the alteration, and a first donor plasmid comprising a HPRT nucleic acid sequence that corrects the alteration and that lacks a sequence complementary to the sequence of first and second gRNA that hybridizes to the HPRT gene, and then culturing the cell in a medium comprising hypoxanthine-aminopterin-thymidine (HAT);
   c) transfecting the cell with a third gRNA that hybridizes to the HPRT gene, thereby re-introducing the alteration to the HPRT gene, and then culturing the cell in a medium comprising 6-thioguanine; and
   d) co-transfecting the cell with a gRNA that hybridizes to a nucleic acid sequence of a subsequent target gene, a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT; or
   e) co-transfecting the cell with a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT.

2. The method according to claim 1, further comprising repeating step c), and thereafter repeating steps b) through d) a plurality of times, wherein the target gene in step b) is a different gene each time step b) is repeated and wherein the subsequent target gene in step d) is both different from the target gene in step b) and is a different gene each time step d) is repeated.

3. The method according to claim 1, wherein the Cas9-competent cell comprises Cas9 integrated into its genome or wherein the Cas9-competent cell has been transfected with a plasmid encoding Cas9.

4. The method according to claim 1, wherein the first donor plasmid comprises the nucleic acid sequence of SEQ ID NO:21 or wherein the second donor plasmid comprises the nucleic acid sequence of SEQ ID NO:22.

5. The method according to claim 1, wherein the HPRT nucleic acid sequence that corrects the alteration and that lacks a sequence complementary to the sequence of first and second gRNA that hybridizes to the HPRT gene comprises the nucleic acid sequence of SEQ ID NO:23.

6. The method according to claim 1, wherein the wild type HPRT nucleic acid sequence comprises the nucleic acid sequence of SEQ ID NO:24.

7. A method comprising:
a) co-transfecting a Cas9-competent cell with a guide RNA (gRNA) that hybridizes to a nucleic acid sequence of a target gene and a first gRNA that hybridizes to a nucleic acid sequence of the HPRT gene, thereby introducing an alteration to the HPRT gene, and then culturing the cell in a medium comprising 6-thioguanine;
b) co-transfecting the cell with a second gRNA that hybridizes to the HPRT gene upstream of the alteration, a third gRNA that hybridizes to the HPRT gene downstream of the alteration, and a first donor plasmid comprising a HPRT nucleic acid sequence that corrects the alteration but lacks a sequence complementary to the sequence of second and third gRNA, and optionally, a guide RNA (gRNA) that hybridizes to a nucleic acid sequence of a subsequent target gene, and then culturing the cell in a medium comprising HAT;
c) co-transfecting the cell with the first gRNA, thereby re-introducing the alteration to the HPRT gene, and a gRNA that hybridizes to a nucleic acid sequence of a subsequent target gene, and then culturing the cell in a medium comprising 6-thioguanine; and
d) co-transfecting the cell with a fourth gRNA that hybridizes to the HPRT gene upstream of the alteration, a fifth gRNA that hybridizes to the HPRT gene downstream of the alteration, and a second donor plasmid comprising a HPRT nucleic acid sequence comprising a wild type HPRT nucleic acid sequence that corrects the alteration, and optionally a guide RNA (gRNA) that hybridizes to a nucleic acid sequence of a subsequent target gene, and then culturing the cell in a medium comprising HAT.

8. The method according to claim 7, further comprising e) repeating step c) and thereafter repeating steps b) through d) and, optionally, repeating step e) a plurality of additional times.

9. The method according to claim 8, wherein the subsequent target gene in step c) is a different gene each time step c) is repeated and wherein each subsequent target gene in step c) is different from the target gene in step a).

10. The method according to claim 7, wherein the Cas9-competent cell comprises Cas9 integrated into its genome or wherein the Cas9-competent cell has been transfected with a plasmid encoding Cas9.

11. The method according to claim 7, wherein the first donor plasmid comprises the nucleic acid sequence of SEQ ID NO:21 or wherein the second donor plasmid comprises the nucleic acid sequence of SEQ ID NO:22.

12. The method according to claim 7, wherein the HPRT nucleic acid sequence that corrects the alteration but lacks a sequence complementary to the sequence of second and third gRNA comprises the nucleic acid sequence of SEQ ID NO:23.

13. The method according to claim 7, wherein the wild type HPRT nucleic acid sequence comprises the nucleic acid sequence of SEQ ID NO:24.

14. A method comprising:
a) providing a Cas9-competent cell comprising a hypoxanthine guanine phosphoribosyl transferase (HPRT) gene comprising an alteration;
b) co-transfecting the cell with a first guide RNA (gRNA) that hybridizes upstream of a nucleic acid sequence of a target gene, a second gRNA that hybridizes downstream of the nucleic acid sequence of the target gene, a first donor plasmid comprising a nucleic acid sequence that alters the nucleic acid sequence of the target gene, a first gRNA that hybridizes to the HPRT gene upstream of the alteration, a second gRNA that hybridizes to the HPRT gene downstream of the alteration, and a first donor plasmid comprising a HPRT nucleic acid sequence that corrects the alteration and that lacks a sequence complementary to the sequence of first and second gRNA that hybridizes to the HPRT gene, and then culturing the cell in a medium comprising hypoxanthine-aminopterin-thymidine (HAT);
c) transfecting the cell with a third gRNA that hybridizes to the HPRT gene, thereby re-introducing the alteration to the HPRT gene, and then culturing the cell in a medium comprising 6-thioguanine; and
d) co-transfecting the cell with a first gRNA that hybridizes upstream of a nucleic acid sequence of a subsequent target gene, a second gRNA that hybridizes downstream of the nucleic acid sequence of the subsequent target gene, and a first donor plasmid comprising a nucleic acid sequence that alters the nucleic acid sequence of the subsequent target gene, a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT; or
e) co-transfecting the cell with a fourth gRNA that hybridizes to the HPRT gene upstream of the alteration, a fifth gRNA that hybridizes to the HPRT gene downstream of the alteration, and a second donor plasmid comprising a wild type HPRT nucleic acid sequence that corrects the alteration, thereby restoring the HPRT gene to its wild type form, and then culturing the cell in a medium comprising HAT.

15. The method according to claim 14, further comprising repeating step c), and thereafter repeating steps b) through d) a plurality of times, wherein the target gene in step b) is a different gene each time step b) is repeated and wherein the subsequent target gene in step d) is both different from the target gene in step b) and is a different gene each time step d) is repeated.

16. The method according to claim 14, wherein the Cas9-competent cell comprises Cas9 integrated into its genome or wherein the Cas9-competent cell has been transfected with a plasmid encoding Cas9.

17. The method according to claim 14, wherein the first donor plasmid comprising a HPRT nucleic acid sequence that corrects the alteration comprises the nucleic acid sequence of SEQ ID NO:21.

18. The method according to claim 14, wherein the second donor plasmid comprising a HPRT nucleic acid sequence that corrects the alteration comprises the nucleic acid sequence of SEQ ID NO:22.

19. The method according to claim 14, wherein the HPRT nucleic acid sequence that corrects the alteration and that lacks a sequence complementary to the sequence of first and second gRNA that hybridizes to the HPRT gene comprises the nucleic acid sequence of SEQ ID NO:23.

20. The method according to claim 14, wherein the wild type HPRT nucleic acid sequence comprises the nucleic acid sequence of SEQ ID NO:24.

\* \* \* \* \*

UNITED STATES PATENT AND TRADEMARK OFFICE
CERTIFICATE OF CORRECTION

PATENT NO. : 10,724,051 B2
APPLICATION NO. : 15/726531
DATED : July 28, 2020
INVENTOR(S) : Hong Yan and Shuren Liao It is certified that error appears in the above-identified patent and that said Letters Patent is hereby corrected as shown below:

In the Specification

In the STATEMENT OF GOVERNMENT SUPPORT, Column 1, Lines 11-15 should read:
-- This invention was made with government support under R01 GM057962 awarded by the National Institutes of Health. The government has certain rights in the invention. --

Signed and Sealed this
Twenty-first Day of November, 2023

Katherine Kelly Vidal
*Director of the United States Patent and Trademark Office*